(12) United States Patent
Bonabeau et al.

(10) Patent No.: US 8,117,139 B2
(45) Date of Patent: *Feb. 14, 2012

(54) METHODS AND SYSTEMS FOR INTERACTIVE EVOLUTIONARY COMPUTING (IEC)

(75) Inventors: Eric Bonabeau, Winchester, MA (US); Carl Anderson, College Park, MD (US); Belinda Orme, Aldridge (GB); Pablo Funes, Somerville, MA (US); Oliver Bandte, Watertown, MA (US); Mark Sullivan, Houston, TX (US); Sergey Malinchik, Natick, MA (US); Joseph Rothermich, Boston, MA (US)

(73) Assignee: Icosystem Corporation, Cambridge, MA (US)

( * ) Notice: Subject to any disclaimer, the term of this patent is extended or adjusted under 35 U.S.C. 154(b) by 213 days.

This patent is subject to a terminal disclaimer.

(21) Appl. No.: 12/578,395

(22) Filed: Oct. 13, 2009

(65) Prior Publication Data

US 2010/0199186 A1 Aug. 5, 2010

Related U.S. Application Data

(63) Continuation of application No. 11/382,180, filed on May 8, 2006, now Pat. No. 7,603,326, which is a continuation of application No. 10/815,321, filed on Apr. 1, 2004, now Pat. No. 7,043,463.

(60) Provisional application No. 60/460,434, filed on Apr. 4, 2003, provisional application No. 60/491,703, filed on Aug. 1, 2003, provisional application No. 60/506,412, filed on Sep. 26, 2003, provisional application No. 60/523,058, filed on Nov. 18, 2003, provisional application No. 60/534,604, filed on Jan. 6, 2004, provisional application No. 60/537,761, filed on Jan. 20, 2004, provisional application No. 60/539,230, filed on Jan. 26, 2004.

(51) Int. Cl.
G06F 15/18 (2006.01)
G06N 3/00 (2006.01)
G06N 3/12 (2006.01)

(52) U.S. Cl. .......................................... 706/13
(58) Field of Classification Search ................ 706/13
See application file for complete search history.

(56) References Cited

U.S. PATENT DOCUMENTS 4,700,295 A 10/1987 Katsof et al.
(Continued)

FOREIGN PATENT DOCUMENTS

EP 1235180 8/2002
(Continued)

OTHER PUBLICATIONS

Chen, Hsinchun, "Machine Learning for Information Retrievel: Neural Networks, Symbolic Learning, and Genetic Algorithms", Journal of the American society for Information Science, 1995 46(3): pp. 195-216.

(Continued)

*Primary Examiner* — Michael B Holmes
(74) *Attorney, Agent, or Firm* — Morse, Barnes-Brown & Pendleton, P.C.; Sean D. Detweiler, Esq.

(57) ABSTRACT

Methods and systems for interactive evolutionary computing may include generating a set of candidate molecules based on an evolutionary scheme in which an objective function is a priori mathematically unexpressed, presenting data based on the set of candidate molecules to one or more users, receiving at least one input from the user(s), the input(s) based on the user(s)'s evaluation of the presented set of candidate molecules, and, based on the input(s), using at least the evolutionary scheme and the input(s) to generate an updated set of candidate molecules, and repeating the presenting and receiving.

26 Claims, 13 Drawing Sheets

U.S. PATENT DOCUMENTS

| | | |
|---|---|---|
| 4,796,194 A | 1/1989 | Atherton |
| 4,935,877 A | 6/1990 | Koza |
| 5,041,972 A | 8/1991 | Frost |
| 5,136,686 A | 8/1992 | Koza |
| 5,148,513 A | 9/1992 | Koza et al. |
| 5,195,172 A | 3/1993 | Elad et al. |
| 5,231,778 A | 8/1993 | Belobraydich et al. |
| 5,233,513 A | 8/1993 | Doyle |
| 5,428,712 A | 6/1995 | Elad et al. |
| 5,438,782 A | 8/1995 | Belobraydich et al. |
| 5,465,221 A | 11/1995 | Merat et al. |
| 5,541,835 A | 7/1996 | Dextraze et al. |
| 5,568,590 A | 10/1996 | Tolson |
| 5,581,657 A | 12/1996 | Lyon |
| 5,617,510 A | 4/1997 | Keyrouz et al. |
| 5,708,774 A | 1/1998 | Boden |
| 5,737,581 A | 4/1998 | Keane |
| 5,761,381 A | 6/1998 | Arci et al. |
| 5,761,494 A | 6/1998 | Smedley et al. |
| 5,793,931 A | 8/1998 | Hillis |
| 5,799,304 A | 8/1998 | Miller |
| 5,809,489 A | 9/1998 | Davidor et al. |
| 5,855,015 A | 12/1998 | Shoham |
| 5,858,462 A | 1/1999 | Yamazaki et al. |
| 5,864,633 A | 1/1999 | Opsal et al. |
| 5,867,397 A | 2/1999 | Koza et al. |
| 5,890,133 A | 3/1999 | Ernst et al. |
| 5,890,146 A | 3/1999 | Wavish et al. |
| 5,897,629 A | 4/1999 | Shinagawa et al. |
| 5,930,780 A | 7/1999 | Hughes et al. |
| 5,963,447 A | 10/1999 | Kohn et al. |
| 5,963,939 A | 10/1999 | McCann et al. |
| 5,970,487 A | 10/1999 | Shackleford et al. |
| 5,978,507 A | 11/1999 | Shackleton et al. |
| 5,987,457 A | 11/1999 | Ballard |
| 6,029,139 A | 2/2000 | Cunningham et al. |
| 6,055,523 A | 4/2000 | Hillis |
| 6,088,690 A | 7/2000 | Gounares et al. |
| 6,094,652 A | 7/2000 | Faisal |
| 6,098,059 A | 8/2000 | Nordin et al. |
| 6,125,351 A | 9/2000 | Kauffman |
| 6,148,274 A | 11/2000 | Watanabe et al. |
| 6,185,548 B1 | 2/2001 | Schwartz et al. |
| 6,236,955 B1 | 5/2001 | Summers |
| 6,249,714 B1 | 6/2001 | Hocaoglu et al. |
| 6,253,200 B1 | 6/2001 | Smedley et al. |
| 6,282,527 B1 | 8/2001 | Gounares et al. |
| 6,321,205 B1 | 11/2001 | Eder |
| 6,327,582 B1 | 12/2001 | Worzel |
| 6,336,110 B1 | 1/2002 | Tamura et al. |
| 6,349,238 B1 | 2/2002 | Gabbita et al. |
| 6,353,825 B1 | 3/2002 | Ponte |
| 6,408,263 B1 | 6/2002 | Summers |
| 6,411,373 B1 | 6/2002 | Garside et al. |
| 6,424,358 B1 | 7/2002 | DiDomizio et al. |
| 6,430,545 B1 | 8/2002 | Honarvar et al. |
| 6,434,435 B1 | 8/2002 | Tubel et al. |
| 6,434,492 B1 | 8/2002 | Pollack et al. |
| 6,434,542 B1 | 8/2002 | Farmen et al. |
| 6,449,761 B1 | 9/2002 | Greidinger et al. |
| 6,468,770 B1 | 10/2002 | Keyes et al. |
| 6,480,832 B2 | 11/2002 | Nakisa et al. |
| 6,484,166 B1 | 11/2002 | Maynard |
| 6,490,566 B1 | 12/2002 | Schmidt |
| 6,513,024 B1 | 1/2003 | Li |
| 6,523,016 B1 | 2/2003 | Michalski |
| 6,528,715 B1 | 3/2003 | Gargi |
| 6,571,282 B1 | 5/2003 | Bowman-Amuah |
| 6,576,919 B1 | 6/2003 | Yoshida et al. |
| 6,636,848 B1 | 10/2003 | Aridor et al. |
| 6,662,167 B1 | 12/2003 | Xiao |
| 6,671,628 B2 | 12/2003 | Hurst |
| 6,678,618 B1 | 1/2004 | Schwartz et al. |
| 6,709,330 B1 | 3/2004 | Klein et al. |
| 6,718,363 B1 | 4/2004 | Ponte |
| 6,721,647 B1 | 4/2004 | Kita et al. |
| 6,741,959 B1 | 5/2004 | Kaiser |
| 6,745,184 B1 | 6/2004 | Choi et al. |
| 6,760,335 B1 | 7/2004 | Andersson et al. |
| 6,763,354 B2 | 7/2004 | Hosken et al. |
| 6,848,104 B1 | 1/2005 | Van Ee et al. |
| 6,865,571 B2 | 3/2005 | Inaba et al. |
| 6,882,988 B2 | 4/2005 | Subbu et al. |
| 6,895,286 B2 | 5/2005 | Kaji et al. |
| 6,895,396 B2 | 5/2005 | Schwartz et al. |
| 6,895,405 B1 | 5/2005 | Choi et al. |
| 6,904,335 B2 | 6/2005 | Solomon |
| 6,912,587 B1 | 6/2005 | O'Neil |
| 6,928,434 B1 | 8/2005 | Choi et al. |
| 6,934,405 B1 | 8/2005 | Schuessler |
| 6,937,993 B1 | 8/2005 | Gabbita et al. |
| 6,941,287 B1 | 9/2005 | Vaidyanathan et al. |
| 6,941,321 B2 | 9/2005 | Schuetze et al. |
| 6,947,844 B2 | 9/2005 | Steitz et al. |
| 6,947,845 B2 | 9/2005 | Steitz et al. |
| 6,947,930 B2 | 9/2005 | Anick et al. |
| 6,950,270 B2 | 9/2005 | Lyle et al. |
| 6,950,712 B2 | 9/2005 | Ulyanov et al. |
| 6,952,650 B2 | 10/2005 | Steitz et al. |
| 6,952,700 B2 | 10/2005 | Modha et al. |
| 6,957,200 B2 | 10/2005 | Buczak et al. |
| 6,996,560 B1 | 2/2006 | Choi et al. |
| 7,000,700 B2 | 2/2006 | Cairns et al. |
| 7,003,504 B1 | 2/2006 | Angus et al. |
| 7,003,516 B2 | 2/2006 | Dehlinger et al. |
| 7,003,560 B1 | 2/2006 | Mullen et al. |
| 7,007,006 B2 | 2/2006 | Zilio et al. |
| 7,013,238 B1 | 3/2006 | Weare |
| 7,035,740 B2 | 4/2006 | Kermani |
| 7,043,463 B2 | 5/2006 | Bonabeau et al. |
| 7,047,169 B2 | 5/2006 | Pelikan et al. |
| 7,070,647 B2 | 7/2006 | Fujimori et al. |
| 7,076,475 B2 | 7/2006 | Honarvar |
| 7,092,378 B1 | 8/2006 | O'Neil |
| 7,110,888 B1 | 9/2006 | Nicholls |
| 7,117,202 B1 | 10/2006 | Willoughby |
| 7,127,695 B2 | 10/2006 | Huang et al. |
| 7,139,665 B2 | 11/2006 | Datta et al. |
| 7,181,438 B1 | 2/2007 | Szabo |
| 7,190,116 B2 | 3/2007 | Kobayashi et al. |
| 7,191,164 B2 | 3/2007 | Ray et al. |
| 7,194,461 B2 | 3/2007 | Kawatani |
| 7,280,986 B2 | 10/2007 | Goldberg et al. |
| 7,318,057 B2 | 1/2008 | Aridor et al. |
| 7,333,960 B2 | 2/2008 | Bonabeau et al. |
| 7,356,518 B2 | 4/2008 | Bonabeau et al. |
| 7,457,678 B2 | 11/2008 | Smith et al. |
| 7,461,059 B2 | 12/2008 | Richardson et al. |
| 7,475,027 B2 | 1/2009 | Brand |
| 7,491,494 B2 | 2/2009 | Liu et al. |
| 7,593,905 B2 | 9/2009 | He |
| 7,603,325 B2 | 10/2009 | Jacobson |
| 7,603,326 B2 | 10/2009 | Bonabeau et al. |
| 7,624,077 B2 | 11/2009 | Bonabeau et al. |
| 7,664,094 B1 | 2/2010 | O'Neil |
| 7,707,220 B2 | 4/2010 | Bonabeau et al. |
| 7,882,048 B2 | 2/2011 | Bonabeau et al. |
| 7,966,272 B2 | 6/2011 | Bonabeau et al. |
| 2001/0003824 A1 | 6/2001 | Schnier |
| 2002/0073065 A1 | 6/2002 | Inaba et al. |
| 2002/0073079 A1 | 6/2002 | Terheggen |
| 2002/0083031 A1 | 6/2002 | De Varax |
| 2002/0091661 A1 | 7/2002 | Anick et al. |
| 2002/0138481 A1 | 9/2002 | Aggarwal et al. |
| 2002/0156773 A1 | 10/2002 | Hildebrand et al. |
| 2002/0161747 A1 | 10/2002 | Li et al. |
| 2002/0165703 A1 | 11/2002 | Olhofer et al. |
| 2002/0174101 A1 | 11/2002 | Fernley et al. |
| 2002/0174126 A1 | 11/2002 | Britton et al. |
| 2003/0033287 A1 | 2/2003 | Shanahan et al. |
| 2003/0055614 A1 | 3/2003 | Pelikan et al. |
| 2003/0069873 A1 | 4/2003 | Fox et al. |
| 2003/0088458 A1 | 5/2003 | Afeyan et al. |
| 2003/0187950 A1 | 10/2003 | Rising |
| 2004/0010479 A1 | 1/2004 | Ali |
| 2004/0030414 A1 | 2/2004 | Koza et al. |
| 2004/0053690 A1 | 3/2004 | Fogel et al. |

| | | | |
|---|---|---|---|
| 2004/0063604 | A1 | 4/2004 | Behan et al. |
| 2004/0081977 | A1 | 4/2004 | Hsu et al. |
| 2004/0117333 | A1 | 6/2004 | Voudouris et al. |
| 2004/0117355 | A1 | 6/2004 | Lef et al. |
| 2004/0117402 | A1 | 6/2004 | Tateson et al. |
| 2004/0122798 | A1 | 6/2004 | Lin et al. |
| 2004/0133355 | A1 | 7/2004 | Schneider |
| 2004/0139058 | A1 | 7/2004 | Gosby et al. |
| 2004/0162738 | A1 | 8/2004 | Sanders et al. |
| 2004/0172202 | A1 | 9/2004 | Sidorowich |
| 2004/0186827 | A1 | 9/2004 | Annick et al. |
| 2004/0204957 | A1 | 10/2004 | Afeyan et al. |
| 2004/0243388 | A1 | 12/2004 | Corman et al. |
| 2004/0254901 | A1 | 12/2004 | Bonabeau et al. |
| 2005/0005232 | A1 | 1/2005 | Gosby |
| 2005/0010553 | A1 | 1/2005 | Liu |
| 2005/0118612 | A1 | 6/2005 | Bonabeau et al. |
| 2005/0119983 | A1 | 6/2005 | Bonabeau et al. |
| 2005/0131884 | A1 | 6/2005 | Gross et al. |
| 2005/0165763 | A1 | 7/2005 | Li et al. |
| 2005/0177280 | A1 | 8/2005 | Almstetter et al. |
| 2005/0187926 | A1 | 8/2005 | Britton et al. |
| 2005/0198026 | A1 | 9/2005 | Dehlinger et al. |
| 2005/0261953 | A1 | 11/2005 | Malek et al. |
| 2006/0010117 | A1 | 1/2006 | Bonabeau et al. |
| 2006/0010126 | A1 | 1/2006 | Anick et al. |
| 2006/0122861 | A1 | 6/2006 | Scott et al. |
| 2006/0167862 | A1 | 7/2006 | Reisman |
| 2006/0167896 | A1 | 7/2006 | Kapur et al. |
| 2006/0184521 | A1 | 8/2006 | Ponte |
| 2006/0195325 | A1 | 8/2006 | Tateson et al. |
| 2006/0248044 | A1 | 11/2006 | Zhang et al. |
| 2007/0027830 | A1 | 2/2007 | Simons et al. |
| 2007/0067212 | A1 | 3/2007 | Bonabeau et al. |
| 2007/0156677 | A1 | 7/2007 | Szabo |
| 2007/0192263 | A1 | 8/2007 | Zhu |
| 2007/0244870 | A1 | 10/2007 | Laurent et al. |
| 2007/0298866 | A1 | 12/2007 | Bonabeau et al. |
| 2008/0021855 | A1 | 1/2008 | Bonabeau et al. |
| 2008/0040671 | A1 | 2/2008 | Reed |
| 2008/0055049 | A1 | 3/2008 | Weill et al. |
| 2008/0109420 | A1 | 5/2008 | Britton et al. |
| 2008/0255024 | A1 | 10/2008 | Behan et al. |
| 2010/0199186 | A1 | 8/2010 | Bonabeau et al. |
| 2010/0211558 | A1 | 8/2010 | Bonabeau et al. |
| 2011/0137839 | A1 | 6/2011 | Bonabeau et al. |

FOREIGN PATENT DOCUMENTS

| | | |
|---|---|---|
| EP | 1782285 | 5/2007 |
| WO | WO 95/016977 | 6/1995 |
| WO | WO 00/02136 | 1/2000 |
| WO | WO 00/02138 | 1/2000 |
| WO | WO 00/54185 | 9/2000 |
| WO | WO 02/27541 | 4/2002 |
| WO | WO 2006/014454 | 2/2006 |

OTHER PUBLICATIONS

Lopez-Pujalte, Cristine et al., "A Test of Genetic Alrorithms in Relevance Feedback", Information Processing management, 2001, 13 pages.

Honma, Masaki et al., "Knowledge Refinement Approach through Incorporating Case-based Knowledge in Maintenance Engineer Scheduling AI System"; Systems, Man, and Cybernetics, 1999. IEEE SMC '99 Conference Proceedings. 1999 IEEE International Conference on vol. 5, Oct. 12-15, 1999 pp. 814-819 vol. 5.

Ioannidis, Stratos et al. "Fuzzy Supervisory Control of Manufacturing Systems", Robotics and Automation, IEEE Transactions on vol. 20, Issue 3, Jun. 2004 pp. 379-389.

Tao, Yongcai et al., "Adaptive Multi-round Scheduling Strategy for Divisible Workloads in Grid Environments", Information Networking, 2009. ICOIN 2009. International Conference on Jan. 21-24, 2009 pp. 1-5.

Tsourveloudis, Nikos et al., "Work-in-Process Scheduling by Evolutionary Tuned Distributed Fuzzy Controllers", Robotics and Automation, 2006. ICRA 2006 IEEE International Conference on May 15-19, 2006 pp. 1420-1425.

International Search Report for PCT/US09/42594.

Luo, B. et al., *A World Wide Web Based Image Search Engine Using Text and Image Content Features*, Electronic Imaging, SPIE vol. 5018 (2003), pp. 123-130.

Wu, P., et al., *Adaptive Nearest Neighbor Search for Relevance Feedback in Large Image Databases*, MM'01 Sep. 30-Oct. 5, 2001, pp. 89-97.

Guanci, Yang et al.; "Sustainable Genetic Algorithms Basis of Relative Adaptation Strategy and Self-adaptive Learning Operator", 2008 International Symposium on Computational Intelligence and Design, pp. 225-228.

Matsui, K. et al.; "New Selection Method to Improve the Population Diversity n Genetic Algorithms"IEEE SMC '99 Conference Proceedings. 1999 IEEE International Conference, pp. 625-630 vol. 1.

Wu, Yong-Gang et al.; "A Diploid Genetic Approach to Short-Term Scheduling of Hydro-Thermal System", IEEE Transactuions on Power Systems, vol. 15, No. 4, Nov. 2000, pp. 1268-1274.

Yang, Jun-Jie et al.; "A Hybrid Intelligent Messy Genetic Algorithm for Daily Generation Scheduling in Power System", Proceeding of the Third International Conference on Machine Learning and Cybernetics, Shanghai, Aug. 26-29, 2004, pp. 2217-2222, vol. 4.

Office Action for Japanese patent application 2006-524908.

Sheth et al., "Evolving Agents for Personalized Information Filtering", IEEE 1993, pp. 345-352.

Moriyama, et al., "Interactive Parallel Generic Algorithm and Its Characteristic of Convergence", 17th Fuzzy System Symposium, Japan, Sep. 2001.

Owais et al., "Evolutionary Learning of Boolean Queries by Genetic Programming," Conference of Advances in Databases and Information Systems, 2005:54-65.

Takagi, Hideyuki, "Interactive evolutionary computation: fusion of the capabilities of EC optimization and human evaluation." Proc. IEEE 89: 1-23.

Yang et al., "Query Improvement in Information Retrieval Using Genetic Algorithms—A Report on the Experiments of the TREC Project," TREC Book, 1992:31-58.

Anderson et al., "Evolutionary Testing as Both a Testing and Redesign Tool: a Study of a Shipboard Firemain's Valve and Pump Controls," Congress on Evolution Computation, 2004, 1:1089-1097.

Anderson et al., "Modeling, Quantifying and Testing Complex Aggregate Service Chains," Web Services, 2005, 1:274-281.

Ashburn et al., "Interactive Inversion of Financial Markets Agent-Based Models," Congress on Evolutionary Computation, 2004, 1:522-529.

Bäck et al., "Handbook of Evolutionary Computation," Oxford University Press and Publishing Ltd., 1997:14.

Baeza-Yates et al., "Chapter 5: Query Operations," Second Edition of Modern Information Retrieval, Addison-Wesley, 1999:117-139.

Banks, Jerry, "1.7 Steps in a Simulation Study," Handbook of Simulation: Principles, Methodology, Advances, Applications, and Practice, Wiley-Interscience, 1998:15.

Banks, Jerry, "1 Introduction to Simulation," Second Edition of Discrete-Event System Simulation, Prentice-Hall, 1996:3-55.

Banzhaf et al., "Genetic Programming: An Introduction on the Automatic Evolution of Computer Programs and Its Applications," Genetic Programming as Machine Learning, Morgan Kaufmann Publishers, 1997:14.

Beasley et al., "An Introduction to Genetic Algorithms," National Centre for Software Technology, 7(1):3-19.

Bentley et al., "New Trends in Evolutionary Computation," IEEE Congress on Evolutionary Computation, 2001, 1:162-169.

Brunner et al., "Using Semantic Graphs in Clustering Process: Enhance Information Level," IEEE/WIC/ACM, 2004:221-227.

Buchsbaum et al., "Designing Collective Behavior in a Group of Humans Using a Real-Time Polling System and Interactive Evolution," Swarm Intelligence Symposium, 2005:15-21.

Carrano et al., "Electric Distribution Network Multiobjective Design Using a Problem-Specific Genetic Algorithm," IEEE Transactions on Power Delivery, 2006, 21(2):995-1005.

Cho et al., "Multiobjective Optimal Design of Interior Permanent Magnet Synchronous Motors Considering Improved Core Loss Formula," IEEE Transactions on Energy Conversion, 1999, 14(4):1347-1352.

Cordon et al., "Evolutionary Learning of Boolean Queries by Multiobjective Genetic Programming," Spinger-Verlag, 2002:710-719.

Cortinas, Marty, "HPS to remodel Ithink simulator (High Performance Systems Inc's Ithink 5.0 Business-Modeling, Simulation Software)," MacWEEK Product Announcement, 1997, 11(26):29(2).

Cranfield, et al., "Exposure of magnetic bacteria to simulated mobile phone-type RF radiation has no impact on mortality," IEEE Transactions on Nanobioscience, 2003, 2(3):146-149.

De Moor et al., "A Geometrical Approach to Maximal Corank Problems in the Analysis of Linear Relations," 25th IEEE Conference on Decision and Control, 1986, 25:1990-1995.

Esbensen et al., "Design Space Exploration Using the Genetic Algorithm," IEEE International Symposium on Circuit and Systems, 1996, 4:500-503.

Fang et al., "Concurrent Optimization for Parameters of Powertrain and Control System of Hybrid Electric Vehicle Based on Multi-Objective Genetic Algorithms," SICE-ICASE, 2006:2424-2429.

Ferber, Jacques, "Multi-Agent Systems: An Introduction to Distributed Artificial Intelligence," Principles of Multi-Agent Systems, Addison Wesley Longman Limited, 1999:1-48.

Fridman et al., "Robust optimal power control for ad hoc networks," 40th Annual Conference on Information Sciences and Systems, 2006:729-733.

Funes et al., "Interactive Multi-Participant Tour Allocation," Congress on Evolutionary Computation, 2004, 2:1699-1705.

Giacinto et al., "Instanced-Based Relevance Feedback for Image Retrieval," 2004:1-8.

Gopinath et al., "An Integrated Methodology for Multiobjective Optimal Component Placement and Heat Sink Sizing," Components and Packaging Technologies, IEEE Transactions on Components, Packaging and Manufacturing Technology, Part A: Packaging Technologies, 2005, 4(4):869-876.

Guadiano et al., "Evolving Behaviors for a Swarm of Unmanned Air Vehicles," Swarm Intelligence Symposium, Jun. 2005, Publication pp. 317-324.

Guoqiang et al., "Multiobjective Optimization Scheduling Based on Fuzzy Genetic Algorithm in Cascaded Hydroelectric Stations," Transmission and Distribution Conference and Exhibition: IEEE/PES Asia and Pacific, 2005:1-4.

Han et al., "A Multi-Objective Genetic Programming/NARMAX Approach to Chaotic Systems Identification," The 6th World Congress on Intelligent Control and Automation, 2006, 1:1735-1739.

Horng et al., "Applying Genetic Algorithms to Query Optimization in Document Retrieval," Information Processing and Management, 2000, 36:737,759.

Ishibushi et al., "Comparison Between Single-Objective and Multi-Objective Genetic Algorithms: Performance Comparison and Performance Measures," IEEE Congress on Evolutionary Computation, 2006:1143-1150.

Kaltofen et al., "Processor-Efficient Parallel Solution of Linear Systems. II. The Positive Characteristic and Singular Cases," 33rd Annual Symposium on Foundations of Computer Science, 1992:714-723.

Kato et al., "Large Scale Fuzzy Multiobjective 0-1 Programs Through Genetic Algorithms with Decomposition Procedures," Proceedings of 2nd International Conference on Knowledge-Based Intelligent Electronic Systems, 1998, 1:278-284.

Klabbankoh et al., "Applied Genetic Algorithms in Information Retrieval," 1999:1-6.

Kosorukoff, Alex, "Human Based Genetic Algorithm," IEEE International Conference on Systems, Man, and Cybernetics, 2001, 5:3464-3469.

Kraft et al., "The Use of Genetic Programming to build queries for Information Retrieval," IEEE, 1994:468-473.

Kumar et al., "Assessing the Convergence of Rank-Based Multiobjective Genetic Algorithms," 2nd International Conference on Genetic Algorithms in Engineering Systems: Innovations and Applications, 1997:19-23.

Kupinski et al., "Multiobjective genetic optimization of diagnostic classifiers with implications for generating receiver operating characteristic curves," IEEE Transactions on Medical Imaging, 1999, 18(8):675-685.

Linkens et al., "A Distributed Genetic Algorithm for Multivariable Fuzzy Control," IEEE Colloquium on Genetic Algorithms for Control Systems Engineering, Sep. 1-Sep. 3, 1993.

Liu et al., "A Multiobjective Mimetic Algorithm Based on Particle Swarm Optimization," IEEE Transactions on Systems, Man and Cybernetics, 2007, 37(1):42-50.

Lopez-Pujalte et al., "Genetic algorithms in relevance feedback: a second test and new contributions," Information Processing and Management, 2003, 39:669-687.

MacArthur et al., "Relevance Feedback Decision Trees in Content-Based Image Retrieval," Proceedings of IEEE Workshop on Content-Based Access of Image and Video Libraries, 2000:1-5.

MacEachern, L., "Constrained Circuit Optimization Via Library Table Genetic Algorithms," IEEE International Symposium on Circuits and Systems, 1999, 6:310-313.

Malinchik, S., "Interactive Exploratory Data Analysis," Congress on Evolutionary Computation, 2004, 1:1098-1104.

Meilhac et al., "Relevance Feedback and Category Search in Image Databases," 1999:1-7.

Michalewicz, Zbigniew, "Genetic Algorithms + Data Structures = Evolution Programs," Revised and Extended Third Edition of GAs: What Are They?, Springer-Verlag, 1996:13-31.

Micro Saint 3.2 (278548); Micro Analysis & Design Inc., 4900 Pearl East Cir. #201E, Boulder, CO 80301, 1986.

Mingqiang et al., "GA-Based Multi-Objective Optimization," Proceedings of the 3rd World Congress on Intelligent Control and Automation, 2000, 1:637-640.

Moss et al., "Editorial Introduction: Mess Systems—The Target for Multi Agent Based Simulation," Lecture Notes in Artificial Intelligence: Subseries of Lecture Notes in Computer Science: Multi-Agent-Based Simulation, Springer-Verlag, 2000:1-26.

Pathak et al., "Effective Information Retrieval Using Genetic Algorithms based Matching Functions Adaptation," IEEE Proceedings of the 33rd Hawaii International Conference on System Sciences, 2000:1-8. (Accessed online at <http://citeseerx.inst.psu.edu/viewdoc/summary?doi+10.1.1.104> on Nov. 25, 2008.).

Pollack et al., "Coevolutionary Robotics," Evolvable Hardware, Proceedings of the First NASA/DoD Workshop, 1999: 208-216.

Rodriguez-Vazquez et al., "Multi-Objective Genetic Programming for Nonlinear System Identification," Electronics Letters, 1998, 34(9):930-931.

Ronald, S., "Duplicate genotypes in a genetic algorithm," IEEE World Congress on Computational Intelligence, 1998:793-798.

Sakawa et al., "An Interactive Fuzzy Satisficing Method for Multiobjective Nonconvex Programming Problems with Fuzzy Numbers Through Coevolutionary Genetic Algorithms," IEEE Transactions on Systems, Man and Cybernetics, 2001, 31(3):459-467.

Sciascio et al., "Content-Based Image Retrieval Over the Web Using Query by Sketch and Relevance Feedback," Proceedings of the 4th International Conference on Visual Information System, 1999:123-130.

Sim et al., "Application of Vector Optimization Employing Modified Genetic Algorithm to Permanent Magnet Motor Design," IEEE Transactions on Magnetics, 1997, 33(2):1888-1891.

Smith et al., "The use of genetic programming to build Boolean queries for text retrieval through relevance feedback," Journal of Information Science, 1997, 23(6):423-431.

Srinivas et al., "Genetic Algorithms: A Survey," IEEE Service Center, 1994, 27(6):17-26.

Stejic et al., "Genetic algorithm-based relevance feedback for image retrieval using local similarity patterns," Information Processing and Management, 2003, 39:1-23.

Tan et al., "Enhanced Distribution and Exploration for Multiobjective Evolutionary Algorithms," Congress on Evolutionary Computation, 2003, 4:2521-2528.

Tasoulis et al., "The new window density function for efficient evolutionary unsupervised clustering," The IEEE Congress on Evolutionary Computation, 2005, 3:2388-2394.

Then et al., "Genetic Algorithms in Noisy Environment," Proceedings of IEEE International Symposium on Intelligent Control, 1994:225-230.

Trifonov et al., "Resource Allocation for a Distributed Sensor Network," Swarm Intelligence Symposium, 2005:428-431.
Valenzuela, Christine, "A Simple Evolutionary Algorithm for Multi-Objective Optimization (SEAMO)," Evolutionary Computation, 2002, 1:717-722.
Van der Meche, E., "Nevanlinna-Pick Interpolation with Degree Constraint: Complete Parameterization Based on Lyapunov Inequalities," 43rd IEEE Conference on Decision and Control, 2004, 1:411-416.
Van Veldhuizen, David, "Issues in Parallelizing Multiobjective Evolutionary Algorithms for Real World Applications," Proceedings of the 17th Symposium on Applied Computing (ACM), 2002:595-602.
Wang et al., "An Optimization-Based Algorithm for Job Shop Scheduling," University of Connecticut, Dept. of Electrical Engineering, 2004:10.
Xin et al., "Relevance Feedback for Content-Based Image Retrieval Using Bayesian Network," Proceedings of the Pan-Sydney Area Workshop on Visual Information Processing, 2003:1-4.
Yang et al., "Query Optimization in Information Retrieval Using Genetic Algorithms," Proceedings of the 5th International Conference on Genetic Algorithms, 1993:603-613.
Zeigler et al., "Chapter 1: Introduction to Systems Modeling Concepts," Second Edition of Theory of Modeling Simulation: Integrating Discrete Event and Continuous Complex Dynamic Systems, Academic Press, 2000:3-53.
Zhou et al., "Relevance feedback in image retrieval: A comprehensive review," Springer-Verlag, 2003:536-544.
International Search Report for International Application No. PCT/US06/038134, mailed Jun. 16, 2008.
International Search Report for International Application No. PCT/US04/009965, mailed Jul. 6, 2005.
International Search Report for International Application No. PCT/US04/028038, mailed Apr. 25, 2007.
International Search Report for International Application No. PCT/US07/072101, mailed Mar. 5, 2008.
Supplementary European Search Report for Application No. EP 06 81 5835, dated Sep. 4, 2009.
International Search Report for International Application No. PCT/US04/024616, mailed Jun. 12, 2008.
International Search Report for International Application No. PCT/US06/036765, mailed Aug. 29, 2007.
International Search Report for International Application No. PCT/US05/023884, mailed Dec. 12, 2005.
Supplementary European Search Report for Application No. EP 04 74 9609, dated Feb. 23, 2009.
Supplementary European Search Report for Application No. EP 04 78 2505, dated Feb. 24, 2009.
Non-final office action in U.S. Appl. No. 10/815,321, mailed Sep. 23, 2005.
Non-final office action in U.S. Appl. No. 10/903,621, mailed May 31, 2007.
Non-final office action in U.S. Appl. No. 10/903,621, mailed Sep. 20, 2006.
Non-final office action in U.S. Appl. No. 11/176,968, mailed Aug. 3, 2009.
Non-final office action in U.S. Appl. No. 11/176,968, mailed Jan. 28, 2008.
Non-final office action in U.S. Appl. No. 11/176,968, mailed Jul. 13, 2011.
Non-final office action in U.S. Appl. No. 11/176,968, mailed May 6, 2010.
Non-final office action in U.S. Appl. No. 11/382,180, mailed May 28, 2008.
Non-final office action in U.S. Appl. No. 11/534,035, mailed Jan. 4, 2011.
Non-final office action in U.S. Appl. No. 11/534,035, mailed May 28, 2009.
Non-final office action in U.S. Appl. No. 11/768,460, mailed Aug. 30, 2011.
Non-final office action in U.S. Appl. No. 11/768,460, mailed Mar. 15, 2010.
Non-final office action in U.S. Appl. No. 12/014,490, mailed Nov. 19, 2009.
Non-final office action in U.S. Appl. No. 12/766,450, mailed Jul. 8, 2011.
Non-final office action in U.S. Appl. No. 12/766,450, mailed Sep. 29, 2010.
Non-final office action in U.S. Appl. No. 13/014,215, mailed Apr. 21, 2011.
Final office action in U.S. Appl. No. 11/176,968, mailed Dec. 3, 2008.
Final office action in U.S. Appl. No. 11/176,968, mailed Jan. 5, 2011.
Final office action in U.S. Appl. No. 11/534,035, mailed Feb. 22, 2010.
Final office action in U.S. Appl. No. 11/768,460, mailed Nov. 26, 2010.
Final office action in U.S. Appl. No. 11/534,035, mailed Sep. 6, 2011.
Notice of allowance in U.S. Appl. No. 10/815,321, mailed Dec. 14, 2005.
Notice of allowance in U.S. Appl. No. 10/903,621, mailed Sep. 25, 2007.
Notice of allowance in U.S. Appl. No. 11/382,180, mailed Jun. 17, 2009.
Notice of allowance in U.S. Appl. No. 11/537,143, mailed Dec. 17, 2009.
Notice of allowance in U.S. Appl. No. 12/014,490, mailed Nov. 3, 2010.
Interview summary in U.S. Appl. No. 10/815,321, mailed Dec. 14, 2005.
Interview summary in U.S. Appl. No. 10/815,321, mailed Mar. 21, 2005.
Interview summary in U.S. Appl. No. 10/903,621, mailed May 31, 2007.
Interview summary in U.S. Appl. No. 10/922,777, mailed Jul. 16, 2007.
Interview summary in U.S. Appl. No. 10/922,777, mailed Apr. 19, 2007.
Interview summary in U.S. Appl. No. 10/922,777, mailed Apr. 9, 2007.
Interview summary in U.S. Appl. No. 11/846,267, mailed Dec. 5, 2008.

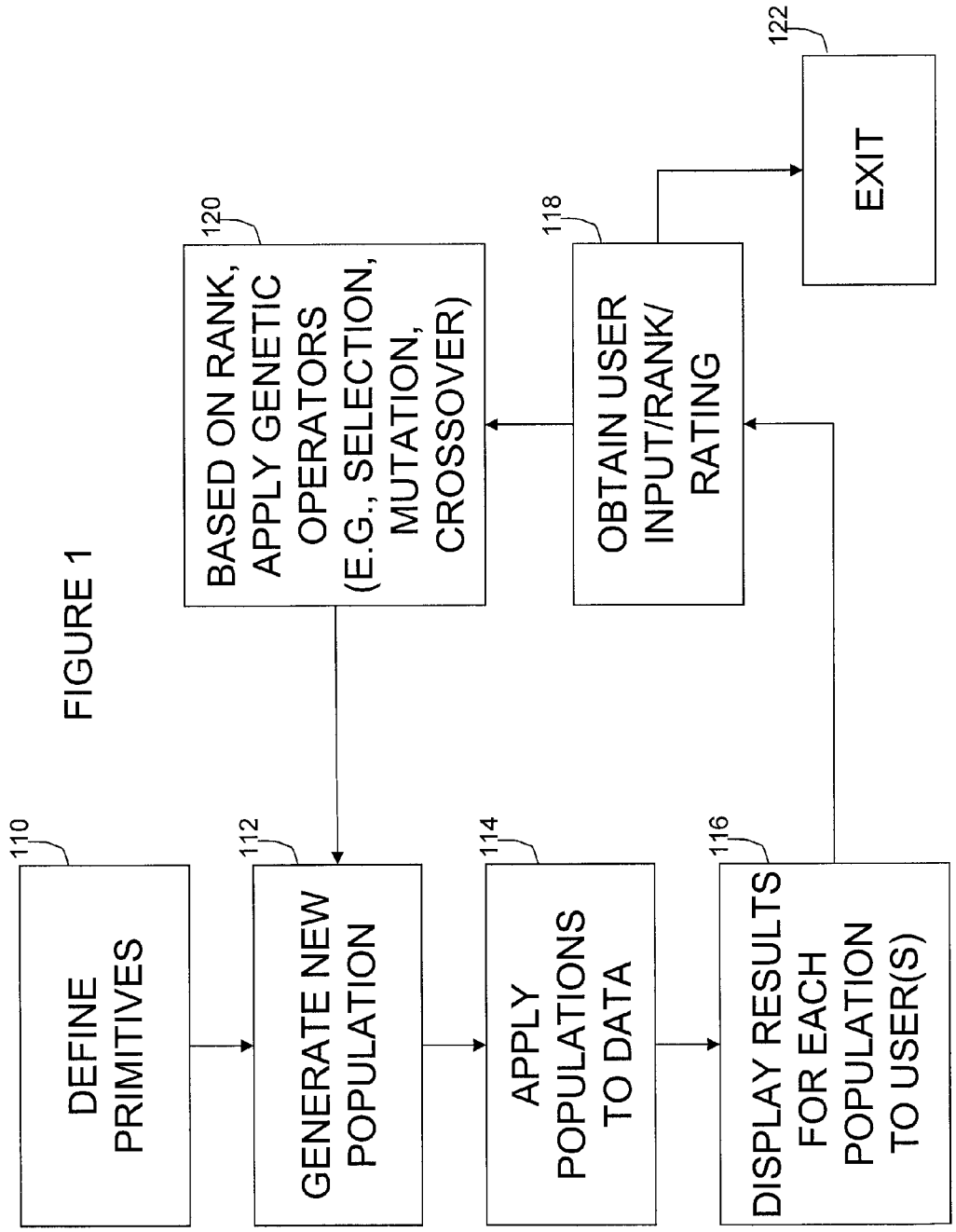

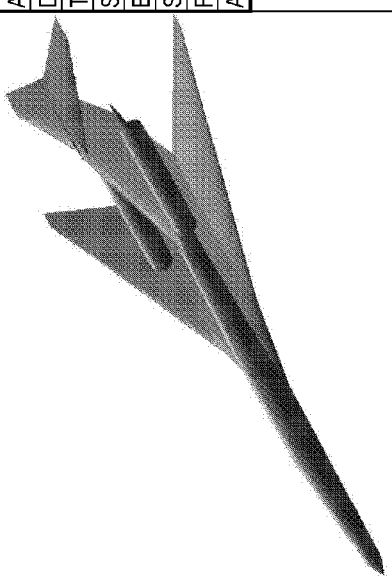

| Iteration: Set-Up | Project: Supersonic Business Jet |
|---|---|

| Objectives | | | | Constraints | |
|---|---|---|---|---|---|
| Name | Preference | Form Factor | | Name | Constraint |
| Acquisition Cost (Mill 2002 $) | 0.2 | 90 | | Sideline Noise (dB) | < 95 |
| Direct Operating Cost ($/SM) | 0.1 | 1.5 | | Flyover noise (dB) | < 88 |
| Take-Off Gross Weight (lbs) | 0.1 | 200000 | | Approach Speed (kts) | <150 |
| Specific Fuel Consumption (lbs/lbs/hr) | 0.1 | 1.2 | | Landing Field Length (ft) | < 9000 |
| Boom Loudness (dB) | 0.2 | 88 | | Take-Off Field Length (ft) | < 9000 |
| Sideline Noise (dB) | 0.1 | 95 | | Max Overpressure (lbs/ft²) | < 0.95 |
| Flyover Noise (dB) | 0.1 | 88 | | Fuel Available (lbs) | >1000 |
| Approach Speed (kts) | 0.1 | 150 | | | |

| General | | | | Wing | | | | Fuselage | | | | Empennage | | | | Engine | | |
|---|---|---|---|---|---|---|---|---|---|---|---|---|---|---|---|---|---|---|
| Name | Min | Max | | Name | Min | Max | | Name | Min | Max | | Name | Min | Max | | Name | Min | Max |
| # of PAX | 8 | 12 | | Location (ft) | 45 | 47 | | Length (ft) | 135 | 160 | | Location (ft) | 87 | 97 | | Location (ft) | 100 | 110 |
| Manuf. ROI | 6 | 12 | | AR | 2 | 2.5 | | Cabin Loc. (ft) | 36 | 41 | | | | | | OPR | 22 | 29 |
| # of Vehicles | 200 | 500 | | TR | 0.05 | 0.3 | | Cabin Length (ft) | 39 | 50 | | | | | | TIT (degR) | 3300 | 3400 |
| Design Range (nm) | 3500 | 4200 | | Area (ft²) | 2300 | 3100 | | Diameter 1 (ft) | 2.2 | 3 | | | | | | FPR | 2.6 | 3.2 |
| Mach | 1.6 | 1.8 | | Sweep (deg) | 67 | 74 | | Diameter 2 (ft) | 7.2 | 7.6 | | | | | | Throttle Ratio | 1.2 | 1.23 |
| TO Thr Der. | 0.8 | 1 | | F Str-Bod Int. | 0.4 | 0.8 | | Diameter 3 (ft) | 7.2 | 8 | | | | | | T/W Ratio | 0.41 | 0.45 |
| | | | | F Str-Wng Int. | 0.2 | 0.4 | | Diameter 4 (ft) | 7.2 | 7.6 | | | | | | | | |
| | | | | A Str-Bod Int. | 0.4 | 0.6 | | Diameter 5 (ft) | 4.5 | 6.5 | | | | | | | | |
| | | | | A Str-Wng Int. | 0.2 | 0.5 | | Diameter 6 (ft) | 2.3 | 3.1 | | | | | | | | |
| | | | | TCR - root | 0.025 | 0.045 | | | | | | | | | | | | |
| | | | | TCR - tip | 0.025 | 0.045 | | | | | | | | | | | | |
| | | | | Twist - root | -2 | 2 | | | | | | | | | | | | |
| | | | | Twist - tip | 0 | 5 | | | | | | | | | | | | |

Fig. 3

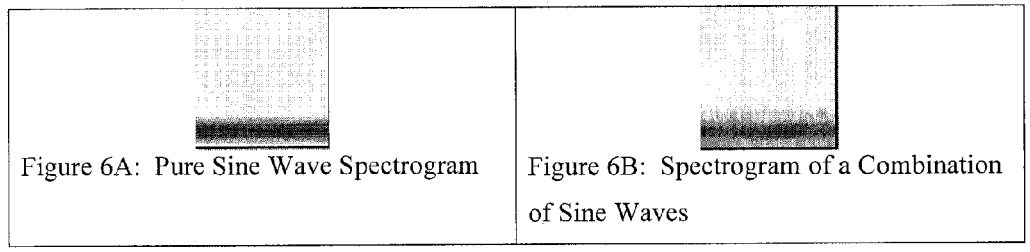
Figure 6A: Pure Sine Wave Spectrogram
Figure 6B: Spectrogram of a Combination of Sine Waves
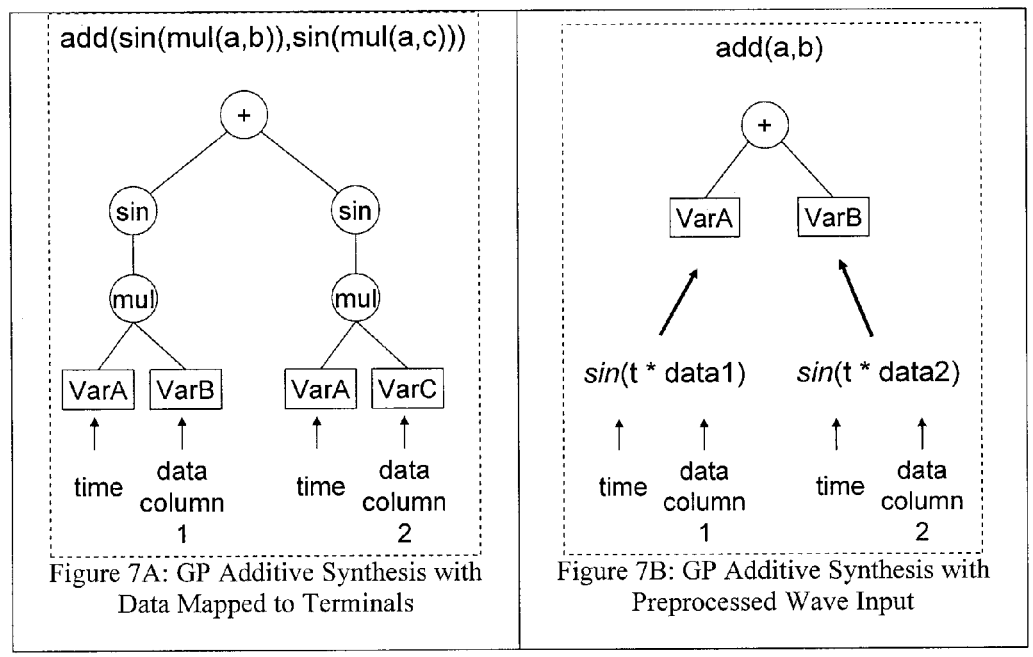
Figure 7A: GP Additive Synthesis with Data Mapped to Terminals
Figure 7B: GP Additive Synthesis with Preprocessed Wave Input

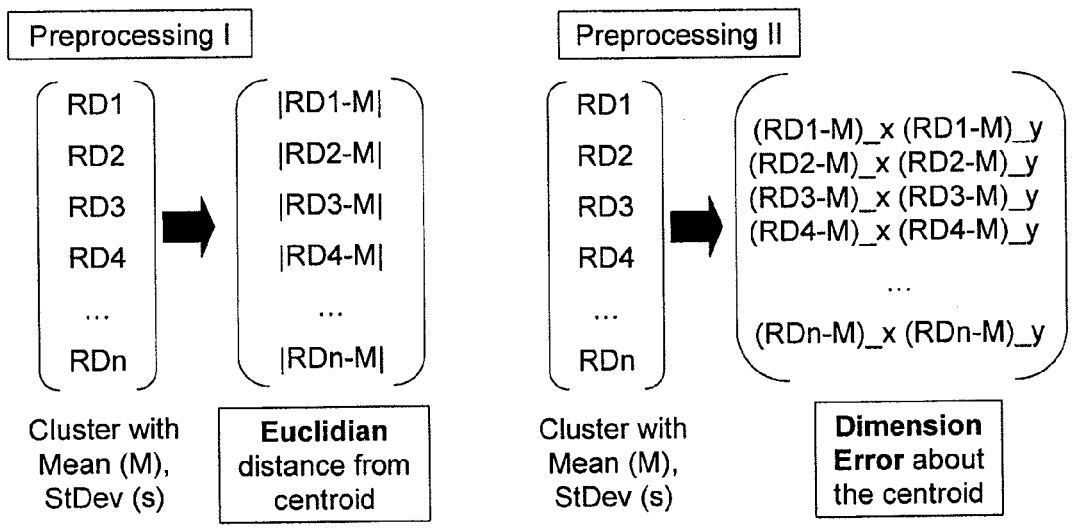
Figures 8A and 8B: Preprocessing for Clusters
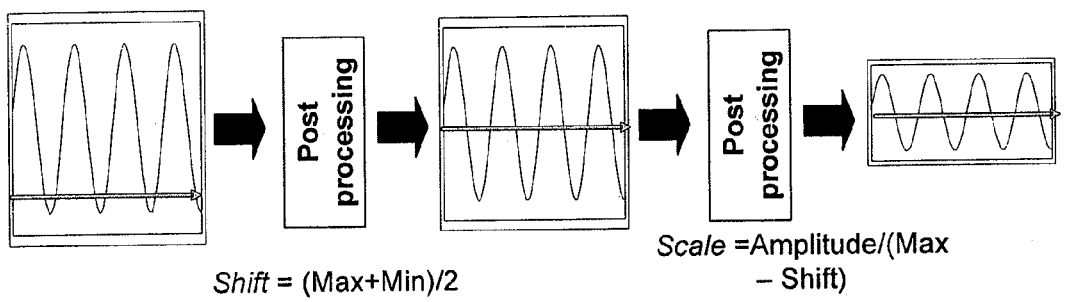
Shift = (Max+Min)/2
Scale = Amplitude/(Max − Shift)
Figure 9: Post Processing of Sound Data $$\begin{bmatrix} 0 & 0 & 0 \\ 0 & 1 & 0 \\ 0 & 0 & 0 \end{bmatrix} \quad \begin{bmatrix} 0 & -1 & 0 \\ -1 & 5 & -1 \\ 0 & -1 & 0 \end{bmatrix} \quad \begin{bmatrix} -2 & -1 & 0 \\ -1 & 1 & 1 \\ 0 & 1 & 2 \end{bmatrix} \quad \begin{bmatrix} 0 & 1 & 0 \\ 1 & -4 & 1 \\ 0 & 1 & 0 \end{bmatrix}$$
Blur  Sharpen  Emboss  Edge Detection
Figure 12: Sample Convolution Kernels
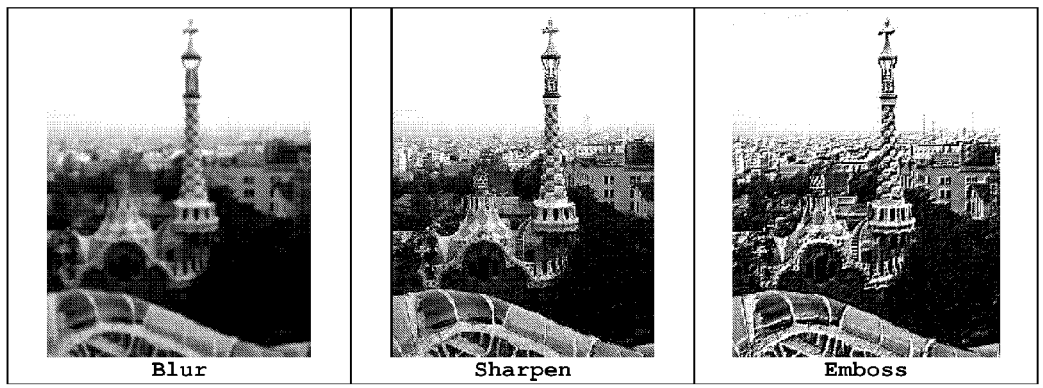
Figure 13: Convolution Filter Examples

METHODS AND SYSTEMS FOR INTERACTIVE EVOLUTIONARY COMPUTING (IEC)

CLAIM OF PRIORITY

This application is a continuation of U.S. application Ser. No. 11/382,180, filed May 8, 2006 and U.S. application Ser. No. 10/815,321, filed Apr. 1, 2004, hereby incorporated herein by reference, which claims the benefit of the following provisional patent applications, the entireties of which are expressly incorporated herein by reference: U.S. Ser. No. 60/460,434 filed on Apr. 4, 2003, U.S. Ser. No. 60/491,703 filed on Aug. 1, 2003, U.S. Ser. No. 60/506,412 filed on Sep. 26, 2003, U.S. Ser. No. 60/523,058 filed Nov. 18, 2003, U.S. Ser. No. 60/534,604 filed Jan. 6, 2004, U.S. Ser. No. 60/537,761 filed on Jan. 20, 2004, and 60/539,230 filed on Jan. 26, 2004.

BACKGROUND (1) Field

The disclosed methods and systems relate generally to interactive evolutionary computing (IEC), and more particularly to IEC embodiments when a fitness or objective function is a priori mathematically unexpressed.

(2) Description of Relevant Art

Evolutionary Algorithms (EA) can be used in solving and/or approximating solutions to multifaceted problems, and/or problems that may change over time. In some embodiments, evolutionary algorithms can generally be understood to include stochastic search methods that replicate natural biological evolution. Accordingly, use of EAs is predicated on an ability to parameterize possible solutions to a problem using a data structure upon which genetic operations can be performed. Those of ordinary skill understand that Genetic Algorithms are an instance of EAs in which the data structure includes a fixed-length list of values (e.g., single bit), where such data structure elements can be referred to as "genes."

Often, evolutionary algorithms operate on a population of potential solutions by applying a "survival of the fittest" principle to produce approximations to a solution, and includes evaluating potential solutions against a prescribed and/or specified objective or fitness function. A new solution set of approximations is thus created at each generation by selecting potential solutions ("individuals") according to their level of "fitness" in the problem domain (i.e., identifying those best approximating the specified fitness function), and breeding these selected "individuals" using operators emulating natural genetics. Such a process facilitates an evolution of populations of "individuals" that are better suited to their environment than the individuals that they were created from, just as in natural adaptation.

Evolutionary algorithms can thus model natural processes including selection, recombination, mutation, migration, locality, and neighborhood. Evolutionary algorithms are generally performed in a parallel manner, using for example, a migration, global, or diffusion model, to operate on populations of individuals rather than single solutions/individuals. Accordingly, a solution set of individuals (e.g., population) can be randomly initialized, and an objective or fitness function can be evaluated for these individuals. If optimization criteria are not met, a new generation is created where individuals are selected according to their fitness for the production of offspring. Parents can be recombined to produce offspring, and offspring can be mutated with a certain probability. The fitness of the offspring is then computed, and the offspring replace the parents in the population to provide a new generation. This cycle is performed until the optimization criteria are reached (e.g., satisfying an error criteria between one or more solutions, and the fitness/objective function). In some embodiments, the fitness/object function may be unknown, and/or a priori, mathematically unexpressed, thereby rendering the aforementioned cycle inoperable.

SUMMARY

Disclosed are method and systems that include generating a solution set based on an evolutionary scheme in which an objective function is a priori mathematically unexpressed, presenting data based on the solution set to one or more users, receiving at least one input from the user(s), the input(s) based on the user(s)'s evaluation of the presented solution set, and, based on the input(s), using at least the evolutionary scheme and the input(s) to generate an updated solution set, and repeating the presenting and receiving. The user input(s) can include a rank of solutions in the solution set, a rating of solutions in the solution set, one or more fitness values, a selection of a solution in the solution set, a selection of a feature of at least one solution in the solution set, a termination of the method, an identification of parents for a genetic algorithm, at least one constraint, a modification of at least one constraint, a modification of at least one genetic operator, and/or a specification of at least one genetic operator. The genetic operator(s) can include selection, crossover, mutation, and/or elitism, and/or variants thereof. The method can be terminated based on the user input(s).

In some embodiments, presenting data based on a solution set to the user(s) can include presenting data based on the solution set in parallel, and presenting data based on the solution set in sequential order. Further, receiving at least one input from the user(s) can include aggregating the at least one input. In one embodiment, receiving the input(s) from the user(s) can include weighting the input(s).

For the disclosed methods and systems, using at least the evolutionary scheme and input(s) to generate an updated solution set can include updating the solution set based on a time since presenting the data to the user(s). Also, using at least the evolutionary scheme and the user(s)'s input(s) to generate an updated solution set can include generating a population based on the evolutionary scheme and the input(s), and, applying the population to at least one data set. In one embodiment, using at least the evolutionary scheme and user(s)'s input(s) to generate an updated solution set includes, based on whether a condition is satisfied, iteratively using the evolutionary scheme and the user(s)'s input(s) to generate an updated solution set before presenting the data based on the solution set to the at least one user. The condition can include, for example, satisfying a number of generations, satisfying a fitness function level, achieving a specified distance between solution alternatives, and/or achieving a diverse population.

In some embodiments, using at least the evolutionary scheme and the user(s)'s input(s) to generate an updated solution set can include applying at least one constraint to the data set(s), and/or weighting the constraint(s), where the weighting can be based on a user associated with the constraint.

In disclosed embodiments, presenting data based on a solution set can includes identifying solutions from the solution set to present to the user(s), where such presented solutions may be a subset of the solution set. Identifying such solutions for presentation can include identifying based on at least one constraint and/or a best fit scheme. The presented data can include collective behavior, at least one physical property a solution(s) in the solution set, a statistical measure(s), and/or a statistical plot(s), for example. As provided herein, the user(s)'s input(s) can be obtained asynchronously. In some embodiments, the methods and systems can include a user(s) modifying a solution(s) of the solution set based on an input(s) from the user(s).

Also disclosed is a system and a computer product having instructions disposed on a computer readable medium, the system and computer product having a processor(s) in communications with a display(s), the processor(s) having instructions for causing the processor(s) to present on the display(s), data based on a solution set to a user(s), the solution set based on an evolutionary scheme in which an objective function is a priori mathematically unexpressed, receive an input(s) from the user(s), the input(s) based on the user(s)'s evaluation of the presented solution set, and, based on the user(s)'s input(s), use at least the evolutionary scheme and the user(s)'s input(s) to generate an updated solution set, and iteratively repeat the present and receive instructions. The system and computer product also include processor instructions for performing other aspects as otherwise disclosed herein.

Other objects and advantages will become apparent hereinafter in view of the specification and drawings.

BRIEF DESCRIPTION OF THE DRAWINGS

FIG. 1 is a block diagram of one example embodiment of the disclosed methods and systems, etc.

FIG. 3 is an example of one user interface for one illustrative embodiment of the disclosed methods and systems;

FIGS. 6A-B show spectrograms related to a sonification embodiment;

FIGS. 7A-B show two embodiments of GP additive synthesis;

FIGS. 8A-B show examples of pre-processing for a sonification embodiment;

FIG. 9 shows examples of post-processing for a sonification embodiment;

FIG. 12 provides illustrative 3×3 convolution kernels for different image processing schemes;

FIG. 13 shows the effects of some convolution kernels on an image; and,

DESCRIPTION

Figure 2A:
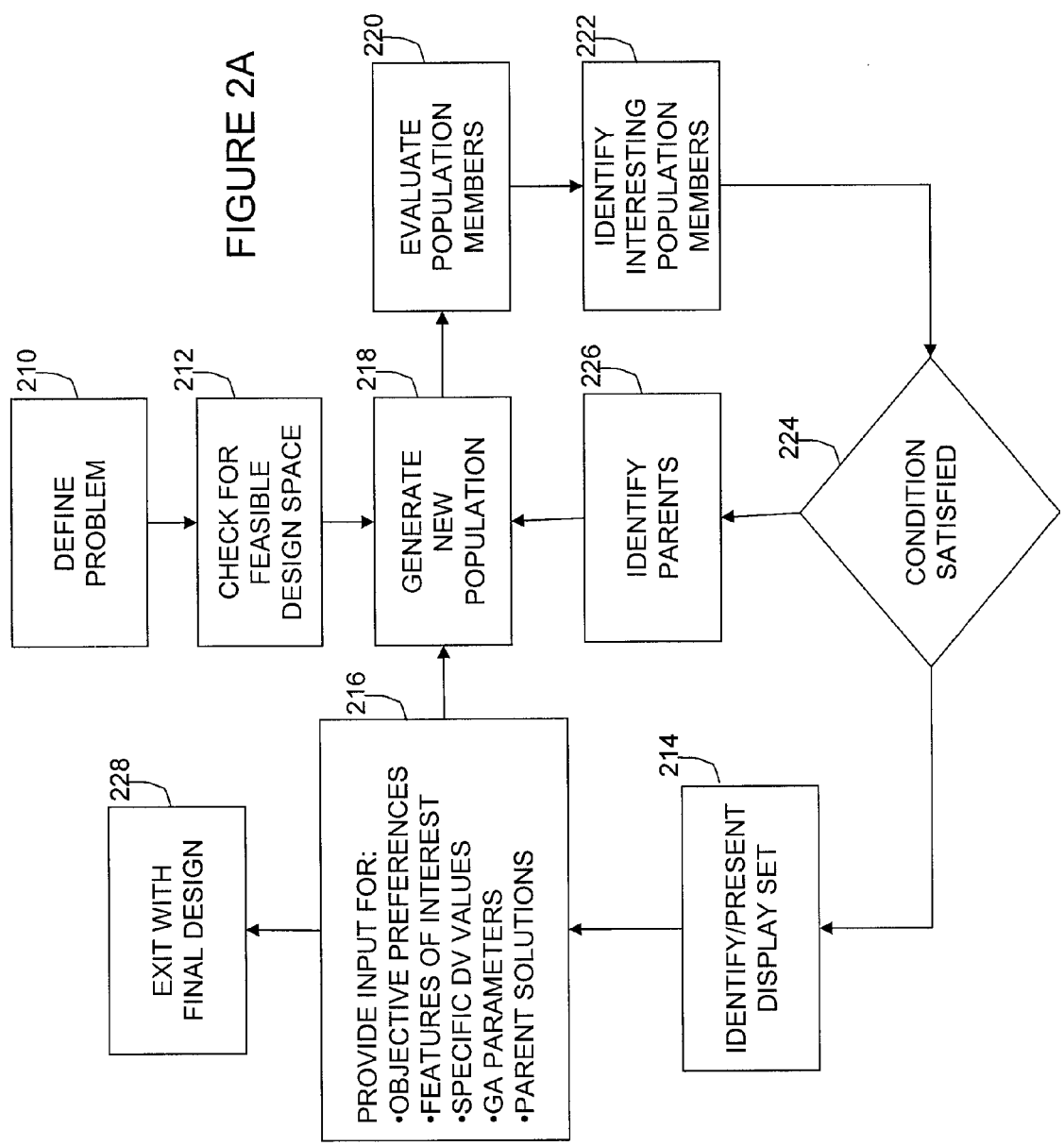
FIGS. 2A-2C show some variations on a second example embodiment of the disclosed methods and systems.

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems or methods of the present disclosure.

The disclosed methods and systems include various EA embodiments for which it may not be possible to encode, describe, or otherwise express a goal or possible solution by a quantifiable fitness and/or objective function, as such criteria may be subjective and/or mathematically difficult and/or complex to quantify (e.g., high order of constraints in defining the objective function). Further, in some of such embodiments, such criteria may be desired to be applied to a collective behavior rather than applied on an individual basis. In some embodiments of the disclosed methods and systems, the evaluation of a solution can be highly subjective. Accordingly, the methods and systems apply evolutionary techniques where the objective function is a priori unspecified, and determined subjectively by a user via the disclosed methods and systems, based on input(s) from the user(s). Whether the objective function (otherwise known as a fitness function) is a priori unknown, incomplete, susceptible to change, and/or a priori unexpressed mathematically, such conditions can be referred to herein collectively as "a priori mathematically unexpressed."

As provided herein, EA (and more specifically, genetic algorithms (GA) and/or genetic programming (GP)) can generally include three factors that include: a population of solutions that may be randomly initialized, one or more mutation operators capable of altering and/or changing at least one of the solutions to a neighboring solution (e.g., a local search operator), and a recombination operator which can recombine a genotype of two parents into a child solution inheriting traits from both parents (e.g., a global search operator). Recombination can include reproduction, mutation, and/or crossover, where crossover can be understood to be the combination of two individuals (the "parents") to produce two more individuals (the "children"). Some embodiments may employ elitism. Those of ordinary skill will recognize that crossover can include asexual crossover and/or single-child crossover. Accordingly, crossover can be understood to provide genetic material from a previous generation to a subsequent generation. Mutation introduces randomness to the process. The variations of EA are thus well known in the art, and the disclosed methods and systems are not limited by such implementations and/or variations of embodiments. It can be understood that using the disclosed methods and systems, via the EA (e.g., GP/GA), a user(s) can guide a search through a specified domain which is often a multi-dimensional domain, to obtain a solution. The user(s)'s input can thus be in the form of modifying operators of the search (e.g., modifying parameters of the EA/GP/GA such as parameters related to mutation and crossover), assigning fitness/ranking to a given set of solutions, and/or by modifying components of a fitness function and/or constraints, for example.

Accordingly, although in some EA applications, a solution can be obtained by comparing individual solutions to a predetermined objective and/or fitness function, in the disclosed embodiments, the objective and/or fitness function is not pre-determined and/or otherwise entirely known (i.e., it is a priori mathematically unexpressed), but rather, such fitness function can be defined, designated, and/or otherwise obtained using the disclosed methods and systems, via user(s) input(s) during iterations and/or epochs of the EA. The user(s) input(s) can be of the type mentioned herein (e.g., modifying EA parameters, assigning rank, modifying components of fitness/constraints).

In some embodiments, a solution is not based on individual solutions (e.g., agents), but rather, a solution can be based on a user-input that can be based on a user-evaluation of the collective population (e.g., swarm). The disclosed methods and systems can thus allow for a collective evaluation of the population by a user, rather than an individual evaluation of population constituents against an objective function. In such embodiments, it can be understood that the disclosed methods and systems may not include an objective function, but rather, a subjective evaluation of the collective behavior of the population.

Because the "search" for a solution is based on user(s) input(s), the disclosed methods and systems allow for several parallel and/or sequential representations of the possible solutions identified in each EA/GA/GP iteration to be visually presented to one or more users. Accordingly, one or more users can be presented (e.g., graphical user interface, display, etc.) with several parallel and/or sequential representations of solutions, and the ability to provide user input via selection tools and modification mechanisms (e.g., sliders, entry boxes, selection/drop-down boxes, etc.). The different users may be provided such solutions at a single processor-controlled device, and/or such users may be connected to multiple processor-controlled devices, for example, over a network. The methods and systems thus contemplate a stand-alone and/or distributed multi-user environment that can include one or more client-server relationships. For example, a user can assign fitness values to the various solutions according to the perceived value or interestingness of the solutions presented to such user. In an embodiment, the user-deemed highest fitness solutions can be selected to make a new generation of offspring solutions, borrowing from the multiplicity of the characteristics in the such user-selected fitness solutions. In a multi-user embodiment, fitness values (and/or other inputs) assigned by the users can be aggregated to the solutions. Aggregation can be performed by weighting fitness values based on the user, and/or applying equal weights to users. For example, user(s) input(s) (e.g., additional constraints and/or other inputs) may be weighted based on the identity, status, etc., of the user (e.g., a supervisor may be provided more weight than a non-supervisor). In one embodiment, fitness values (and/or other inputs) can be weighted based on a user's response time. Those of ordinary skill in the art will recognize that there are many different aggregation and/or weighting mechanisms that can be employed, and the disclosed methods and systems are not limited by such variations.

In some embodiments, multiple users may be given an interval of time in which to respond, and if a response is not received from a given user(s) within the time interval, such user's input(s) may not be employed to obtain a new solution set. The user may or may not be informed of the time interval. In some embodiments, a user's input(s) may be used even though such input(s) was based on a previous generation, and thus, based on the foregoing, the disclosed methods and systems can be understood to allow for asynchronous input of users.

Although the described methods and systems can contemplate a human user, a user can include a non-human user that can be configured with a pattern-recognition mechanism. For example, one embodiment can employ machine vision or other pattern recognition concepts to identify a determined pattern, and cause a selection of a parallel embodiment as provided herein. In some embodiments, visual representations may additionally and/or optionally include not only the agents' collective behavior pattern, but data representing properties and/or characteristics of the collective behavior (e.g., physical and/or other properties, statistical measures, statistical plots, etc.).

FIG. 1 shows one example embodiment of the disclosed methods and systems, where based on the embodiment (e.g., the design being considered, the problem to be addressed, etc.), primitives such as objectives, constraints, fitness evaluation criteria, etc., can be developed 110, and upon which a population of solutions can be developed 112 (e.g., using a genetic algorithm). The solutions can be applied to the data 114 applicable to the embodiment, and at least some of the solutions, and/or data based upon such solutions (e.g., plots, property, characteristic, collective behavior, etc.), can be provided to one or more users 116 for visual inspection. The user can thereafter provide input based on the user's preferences 118, which as provided herein, can be subjective to the user(s), and can include a preference/selection, a ranking, an additional constraint, a modification of a constraint, a selection of a parent, and/or another user input allowed by the embodiment. In the FIG. 1 embodiment, the user input is generally a ranking. Based on the user's input, genetic operations can be performed 120 and a new population generated 112. The example process of FIG. 1 can continue until a user(s) determines that a solution is obtained 122. Those of ordinary skill will understand that the example method and system of FIG. 1 can be rearranged, as provided herein, and for example, can include user input at other additional and/or optional places in the processing.

In a sample embodiment of the FIG. 1 systems and methods, consider a selected design of a paper airplane which may be representative of a user's subjective belief to be approximately the correct relative dimensions for a desired flight trajectory. In a next generation, a user can be provided with parallel configurations, where the selected configuration can remain unchanged, while the designs in other parallel embodiments may mutate based on the rules of the selected embodiment, and/or recombination with a random member of the current generation of embodiments. Accordingly, the determination of a "next" generation is not based solely on evaluation against a single objective function, but rather the subjective expertise of one or more experts selecting an overall fittest design, thereby allowing for a collective evaluation of the solutions (e.g., designs) by experts, rather than an automated evaluation of the solutions (e.g., designs) with respect to a static and explicit objective function. Achievement of a set of primitives to create the desired functionality is thus expedited by the user(s)'s selection procedure. Further, the number of iterations/generations is determined by the users incorporating expert expertise.

Design is commonly understood in the art as the process of identifying solutions to a problem. More specifically the design process aims to discover solutions that satisfy, at least partially, all constraints while optimizing at least one implicit or explicit objective. As provided herein, the disclosed methods and systems can apply Interactive Evolution (IE) to the design process of systems with very large design spaces, in which it may be impractical to explicitly identify a categorical set of relative priorities of objective functions. The expression of a design can assume a number of different forms, from an aesthetic composition to perishable goods to functional equipment to behavioral based rules that generate global behaviors.

Figure 2B:
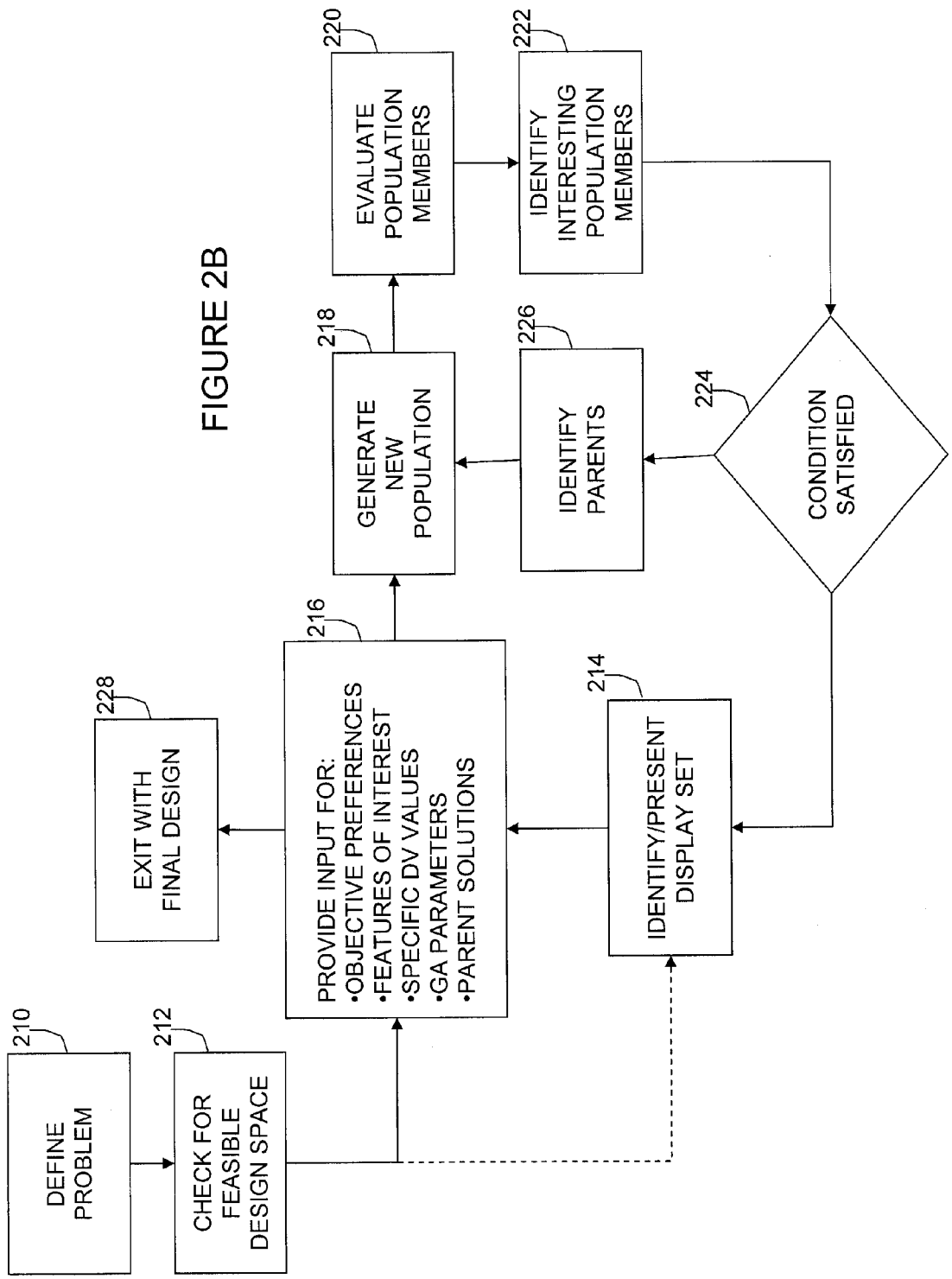
Figure 2C:
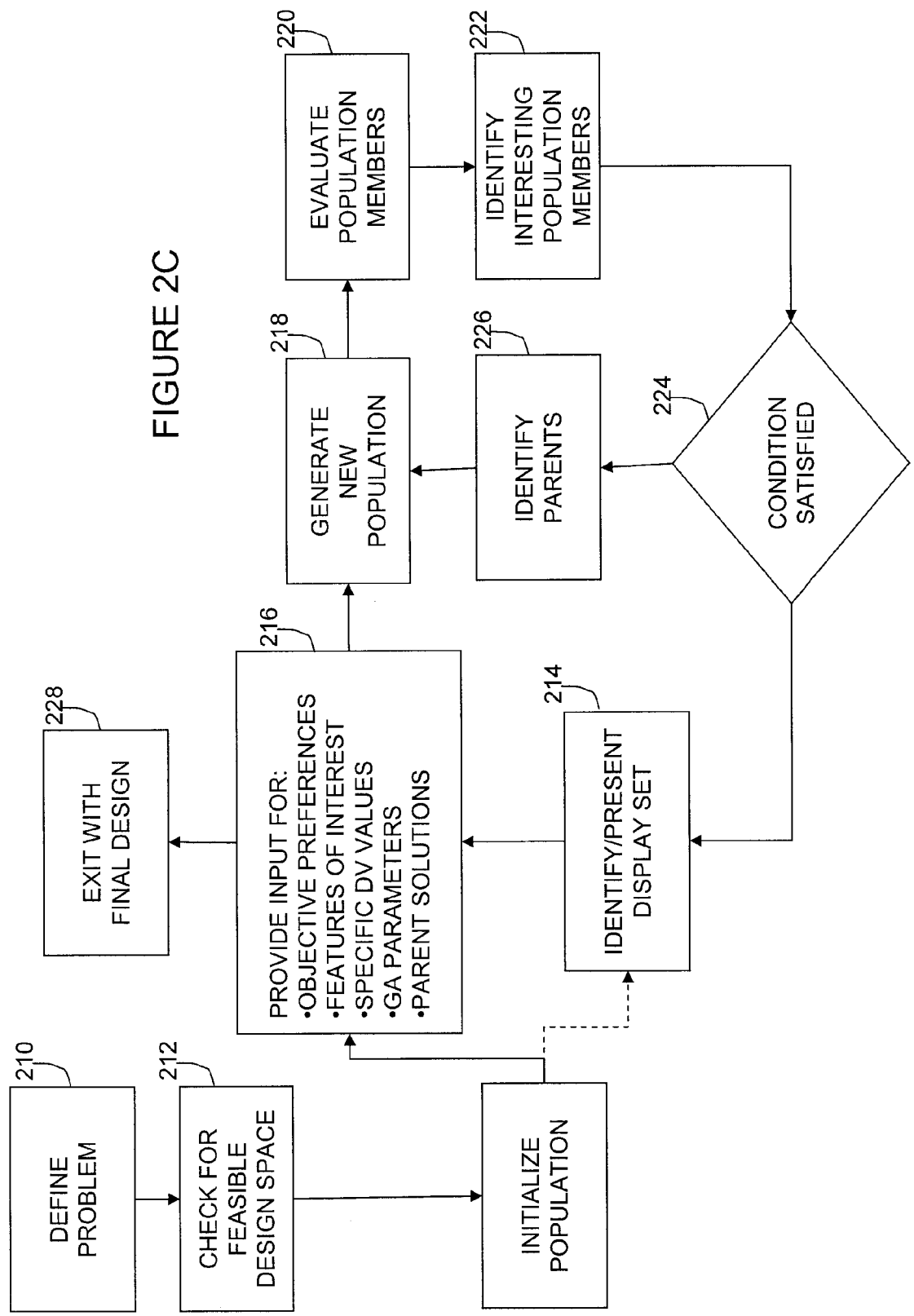

FIGS. 2A-2C show three variations on an example embodiment of the disclosed methods and systems in which user input can be of various forms, and in which a design solution is obtained using the disclosed methods and systems. The three variations are illustrative of the aforementioned ability to rearrange and/or combine different aspects of the disclosed methods, and with like elements numbered identically in the three variations, references herein to "FIG. 2" to include a reference to any one of FIGS. 2A-2C.

The aforementioned design solution can be in response to a design problem, and as the FIG. 2 embodiments indicate, a process can begin by defining a design problem 210 using independent parameters, objectives, constraints, and one or more evaluation functions that describe the objectives' dependencies on the independent parameters. In some embodiments, the design definition can also include identifying a genotype representation of design alternatives, a fitness evaluation scheme that can be influenced by the objectives, and determining procedures for design alternatives that violate constraints.

Further, a design space to search for a solution can be identified 212. One embodiment can identify a design space by testing a random sample, from uniform distributions, of design variable values and determining (e.g., counting) the number of times constraints are violated. For example, if less than ten percent of the random sample satisfies all constraints, constraints may be relaxed and/or new technologies can be introduced to the system, and/or the dependencies of the constraint functions on the design variable settings can be altered.

In the FIG. 2 embodiments, solutions can be generated and thereafter, upon processing described further herein, provided to the designers/users 214, and accordingly, designers can provide input to the system 216 by processing the displayed information and communicating preferences of objectives/solutions, features of interest in particular design alternatives/solutions, whether specific design variables values should be held constant in future iterations, one or more parameter settings the EA should use in the next iteration, and/or whether the design alternatives/solutions should be parents for the next generation. The variations in the information to provide to the designers, and the information to allow designers to affect, can vary based on the design problem/embodiment.

Based on the input from the designer(s), the search/EA can be affected such that new populations of alternatives can be generated 218. Variation operators such as mutation, crossover, weighted average, permutation, and/or representation specific can be used, based on the embodiment, to provide the desired objectives. The generated solution alternatives can then be evaluated 220 based on the design objectives and the constraints to provide constraint and objective values. Those of ordinary skill will understand that various evaluation methods using varying numerical analysis techniques can be used. A subset of design alternatives can be identified 222 based on the different population members' constraint and objective values. Based on whether the designer(s)'s condition (e.g., a number of EA iterations) is satisfied for ending this iteration 224, parents can be identified 226 with a return to generating a new population of alternatives 218, or the set of solutions (and/or data based thereon) can be presented/displayed to the designers 214. The designer condition 224 can include satisfying a specified number of generations in an iteration, reaching a specified fitness/objective function level, establishing a specified (e.g., minimum) distance level between design alternatives, guaranteeing a diverse population, etc., with such conditions provided for illustration and not limitation. As provided previously herein, based on the satisfaction of the condition 224, the solutions (or a subset thereof) can be presented to the designer(s) 214, or new parents can be selected for the EA next generation 226. The new parents can be specified 226 based on the fitness of the population members and/or designer feedback. Further, the presentation of solutions/design alternatives 214 can include a determining, for large objectives, which design alternatives to display. Such down-selecting process can include cluster analysis, displaying representative alternatives based on the objectives and/or design variables, and/or down-selecting based on design alternatives having the highest fitness, with such examples provided for illustration and not limitation.

With reference to the FIG. 2 embodiments, a design solution can be determined 228 based on the designer(s) providing input(s) 216 indicating a solution that satisfies the design requirements. As provided previously herein, the embodiments of FIG. 2 are illustrative, and it can thus be understood that the organization of the processes and schemes of the FIG. 2 embodiments can be further rearranged, combined, expanded, etc., without departing from the scope of the disclosed methods and systems.

In an example embodiment according to FIG. 2, for example, a jet design can be demonstrated using a Genetic Algorithm (GA) with a random starting point as the EA. In the sample embodiment, the GA can be interrupted every eighty generations (e.g., condition 224) to display the current population in the form of pictures with objective values and aircraft configurations. Based on this information, a designer can make choices regarding objective preferences to redirect the EA/search and features of interest to influence selection. For illustrative purposes, only the redirection of the EA/search through objective performances is implemented.

Accordingly with reference to FIG. 2, in a problem definition phase 210 of the example jet design embodiment, five groups of design variables were chosen and displayed, including general variables (e.g., vehicle variables), and geometric parameters for the wing, fuselage, empennage, and engine. The chromosome for the example includes thirty-five variables that can be varied to identify the "best" design (e.g., as provided by the user/designer). A mix of economic, size, and performance parameters were chosen as objectives in the example embodiment, with an emphasis on noise generation. Accordingly, for an initial loop of the FIG. 2 schemes, the Boom Loudness, and Acquisition Cost are provided higher importance (e.g., twenty percent), while other objectives were set at ten percent. Because certain noise levels could be prohibitively large (e.g., fail regulatory approval), some noise objectives had constraints imposed upon them. Other constraints included approach speed, take-off and landing distances, positive amounts of fuel, and/or fuel reserve, for example. Fitness can be computed via a weighted sum of normalized objective values, penalized by a twenty percent increase in value when a constraint is violated. The constraints, objectives, normalization values, and preferences are provided in FIG. 3, and as shown to a designer(s)/user(s).

Determining the amount of feasible design space the constraints allow for searching 212 included executing a large number of random samples (e.g., 10,000) from uniform distributions defined over the design variable ranges. Each sample was evaluated with an analysis tool and a constraint parameter determined. The samples not violating constraints were counted and divided by the total number of samples to yield feasibility as a value between zero and one. In the present example, feasibility was 0.07 percent. By fixing Design Range and Mach Number, feasibility increased to fifty percent.

The GA could then be executed (e.g., FIG. 2, 218, 220, 222, 224) without input from the designer, although in some embodiments, user input can be provided. The GA included a population size of twenty, a elite pool of two, and a probabilistic selection of crossover with one random splice point based on the fitness values of the individuals. Parent solutions were replaced with offspring, and each new member had a fifteen percent probability for mutation at ten genes, sampling a new value from a uniform distribution over the entire range of design variable values.

Figure 4A:
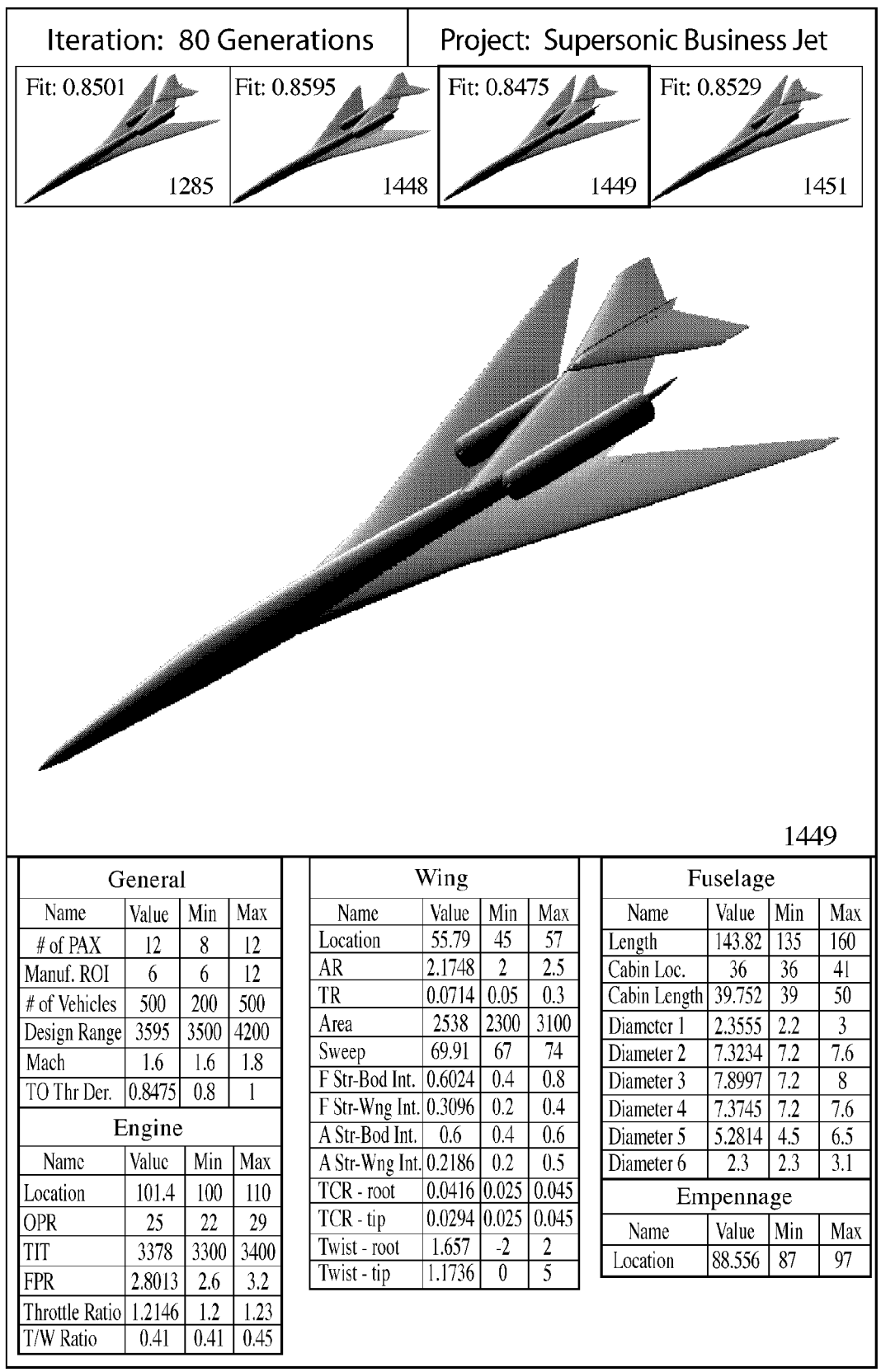
FIGS. 4A-B are a second example of one user interface for one illustrative embodiment of the disclosed methods and systems.
Figure 4B:
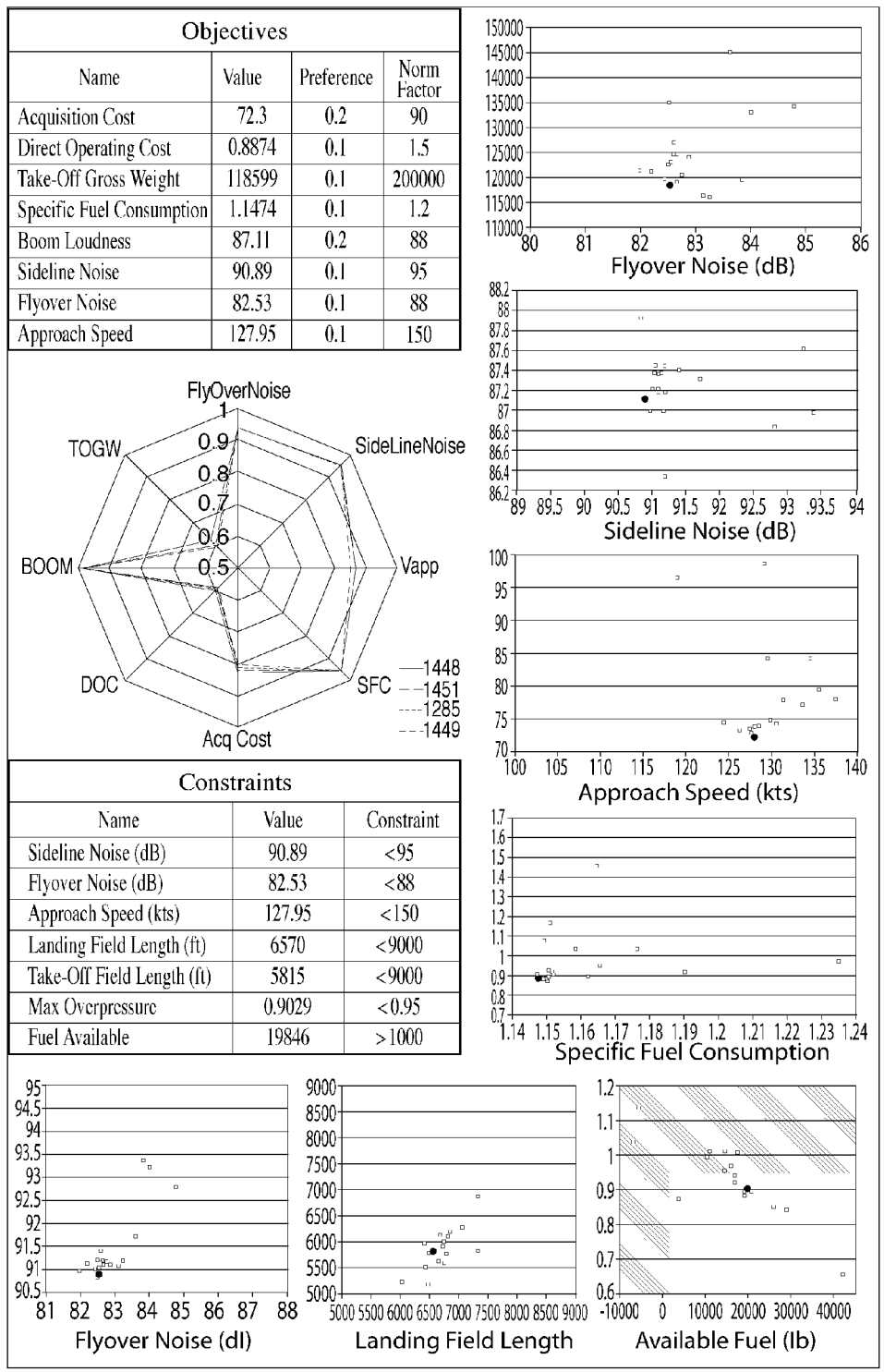

Once the GA exceeded eighty generations (e.g., FIG. 2, 224), the GA was interrupted to display the population of design alternatives 214. In the example embodiment, only four of the solutions were displayed, with those four including the four "best" designs based on fitness and highest diversity in geometrical features. FIGS. 4A and 4B together show an example display provided to a user(s)/designer(s). Chromosome information is provided on the left-hand pane (FIG. 4A). In FIG. 4B, the right-hand panes provide objective and constraint information pertaining to the population and the highlighted design alternative. The top pane presents objective values for the highlighted design alternative, with objective preferences and normalization factors used to generate the fitness values of the present population. The spider graph compares the four alternatives based on normalized objective values, and the right-most four graphs display objective values for the entire population. Below the spider chart is a table of constraint parameter values for the highlighted design alternative and respective constraint values. At the bottom of FIG. 4B are graphs displaying the population with respect to its member's constraint parameter values with the infeasible region superimposed.

A user can thus provide input(s) (e.g., FIG. 2, 216), upon analyzing that all objectives except Boom Loudness were satisfied. Accordingly, in the next iteration of the GA, Boom Loudness' preference can be increased to thirty percent while reducing Acquisition Cost to ten percent. Such input can be provided to the GA by the user via a pop-up window, for example, and although such input redirects the search, selection (e.g., of parent, component, design variable value) is not influenced.

As provided with respect to FIG. 2, the cycle can continue, with the GA executing 218, 220, 222, 224, 226 for eighty generations (e.g., condition, 224) before providing the four best alternatives 214 to the user/designer, and receiving the next user input(s) 216. Upon analysis, a user/designer may change the objectives to satisfy the subjective desires of the designer, and can terminate the process 228 when a design is achieved that satisfies the user's objectives.

It can thus be understood that the example paradigms of FIGS. 1 and 2, where an a priori mathematically unexpressed objective and/or fitness function can be determined based on selections from a user, can be applied to a multitude of applications in a variety of embodiments. For example, the disclosed methods and systems can employ evolutionary schemes and agent-based modeling to facilitate an evolution of rules to cause a population of agents to perform a collective task. The task can be a pattern and/or formation and/or aggregation of the agents, for example. As provided herein, the agents can be initialized with random and/or predefined initial conditions and agent activity in their environment can be based upon one or more rules that can be further based on the activities of one or more of the other agents in the population.

In one embodiment, several parallel configurations and/or embodiments of the methods and systems can be visually presented to a user(s) or another. The visual representation(s) can be used as a basis for creating and/or designing implicit rules leading to and/or otherwise related to the emergence of a collective behavior. It can be understood that the collective behavior can be derived from such rules. The parallel configurations can be varied based on method of visualization (e.g., coloring, relative position, etc.), number of agents, number of agent rules, assignment of agent rules, agent properties and/or attributes (e.g., speed, shape, energy level, etc.), and other factors. As provided herein (e.g., FIG. 1, 118, and/or FIG. 2, 216) a user or another can cause rule evolution by iteratively selecting one of the parallel configurations, where such selected configuration may be subjectively considered by the user to represent a desired collective behavior. Based on the selected configuration or another criteria (e.g., random recombination), other parallel configurations can be generated to provide a new generation of parallel configurations. Such an embodiment may follow a paradigm based on FIG. 1, in which a user input includes a ranking/selection, rather than FIG. 2, in which user inputs may generally be greater in number and sophistication.

The number of generations can be user-determined, and accordingly, the number of generations can be based on a desired collective behavior of the agents and/or properties relating thereto (e.g., problem solving capability). In such an embodiment, the disclosed methods and systems can thus employ agent-based modeling (ABM) and interactive evolution (IE) for effectuating, designing, and/or otherwise causing a collective behavior of autonomous decision-making entities that can be referred to as agents (e.g., "swarm intelligence"). Swarm intelligence can be directed towards collective and/or distributed problem solving without providing centralized control of the agents.

In such an embodiment, the collective behavior can thus be understood to be user-defined, and thus can alter or otherwise be determined, defined, and/or designated based on a user selection and/or other user input. As is known in the art, and as with the various embodiments provided herein, the user-input can be provided in a variety of manners, including selection via a computer mouse, joystick, keyboard, touch-pad, stylus, voice and/or audio command, and other available means for providing an input to a processor-controlled device.

Agent-based modeling (ABM) thus models agents such that an individual agent can assess its situation and can make decisions based upon a set of rules, and therefore, an ABM can be based on a system of agents and the associated relationships between agents. Agents can execute various behaviors based on the system(s) which the agents represent (e.g., producing, consuming, selling, with such examples provided for illustration and not limitation). It can be understood that an ABM can exhibit complex behavior patterns and hence may provide information about the dynamics of the system that the ABM emulates. The system can be an actual (e.g., "real-world") system, or a theoretical system.

For the disclosed embodiment, a solution is thus not based on individual solutions (e.g., agents), but rather, a solution can be based on a user-input that can be based on a user-evaluation of the collective population (e.g., swarm), thereby allowing for a collective evaluation of the population by a user, rather than an individual evaluation of population constituents against an objective function.

In a more specific embodiment of the disclosed methods and systems that is provided for illustration and not limitation, the EA and ABM methods can be integrated to provide methods and systems that facilitate a user-driven methodology for evolving behavior of multiple agents. In the illustrative system, the population can include agents that can be configured to follow and/or otherwise adhere to one of two rules, although those of ordinary skill will understand that other embodiments can use one or more rules. Such rules can be understood herein to be one or more instructions that can be executed by a microprocessor.

In the illustrative system, a selected agent, S, can be randomly associated with two other agents, referred to herein as A (attacker) and B (defender). Further, agent S can be randomly associated with an "aggressor rule" or a "defender" rule. When the association is with the aggressor behavioral rule, S's position changes to maintain a position that positions B between S and A. When S is associated with the defender behavioral rule, S's position changes to maintain a position between A and B. As provided herein, the association of agents S, with attackers and defenders, can be random. Further, the association of agents, S, with an agent rule can similarly be random. In the illustrative system, agents, S, can also be associated with a target point to which the respective agent should move. These target points can be associated with a fixed area, and the target points can be randomly associated with agents. The initial agent locations can also be randomly determined in some embodiments. Those of ordinary skill will understand that the aforementioned random associations and determinations, and/or some of such random associations, may be fixed associations in some embodiments.

In one embodiment of the illustrative system, human-like rules can be applied to the aggressor and/or defender rules (e.g., positioning can be to "block line-of-sight"), regardless of the relative distances between S, A, and B. Those of ordinary skill will recognize that other variations can be used. Other concepts such as collision detection can be implemented to otherwise affect movement of agents.

The methods and systems can also employ parametric rules that can be based on mathematical rules rather than, for example, the aforementioned human-like rules. In parametric embodiments, the positions between S, A, and B can be computationally determined, for example, although such example is provided for illustration and not limitation.

In one embodiment, the rules for a population of N agents can be encoded using a chromosome of length N, where agents can be associated with a number 1–N, and a gene in the chromosome corresponds to and specifies an agent's rule, an associated aggressor agent number, and an associated defender agent number.

The illustrative embodiment of the example system also can include two or more interfaces to observe parallel versions and/or configurations of different configurations and/or embodiments. For the illustrative systems and methods, the parallel versions can allow differing numbers of: agents, "aggressor" agents, "defender" agents, agents following human-like rules, agents following parametric rules, etc. Other options can include varying the speed of agent movement between zero and some predetermined maximum, varying the movement and/or "step" size (e.g., distance) that an agent can move in a given time interval, varying the size of the area in which agents can move, etc.

Figure 5:
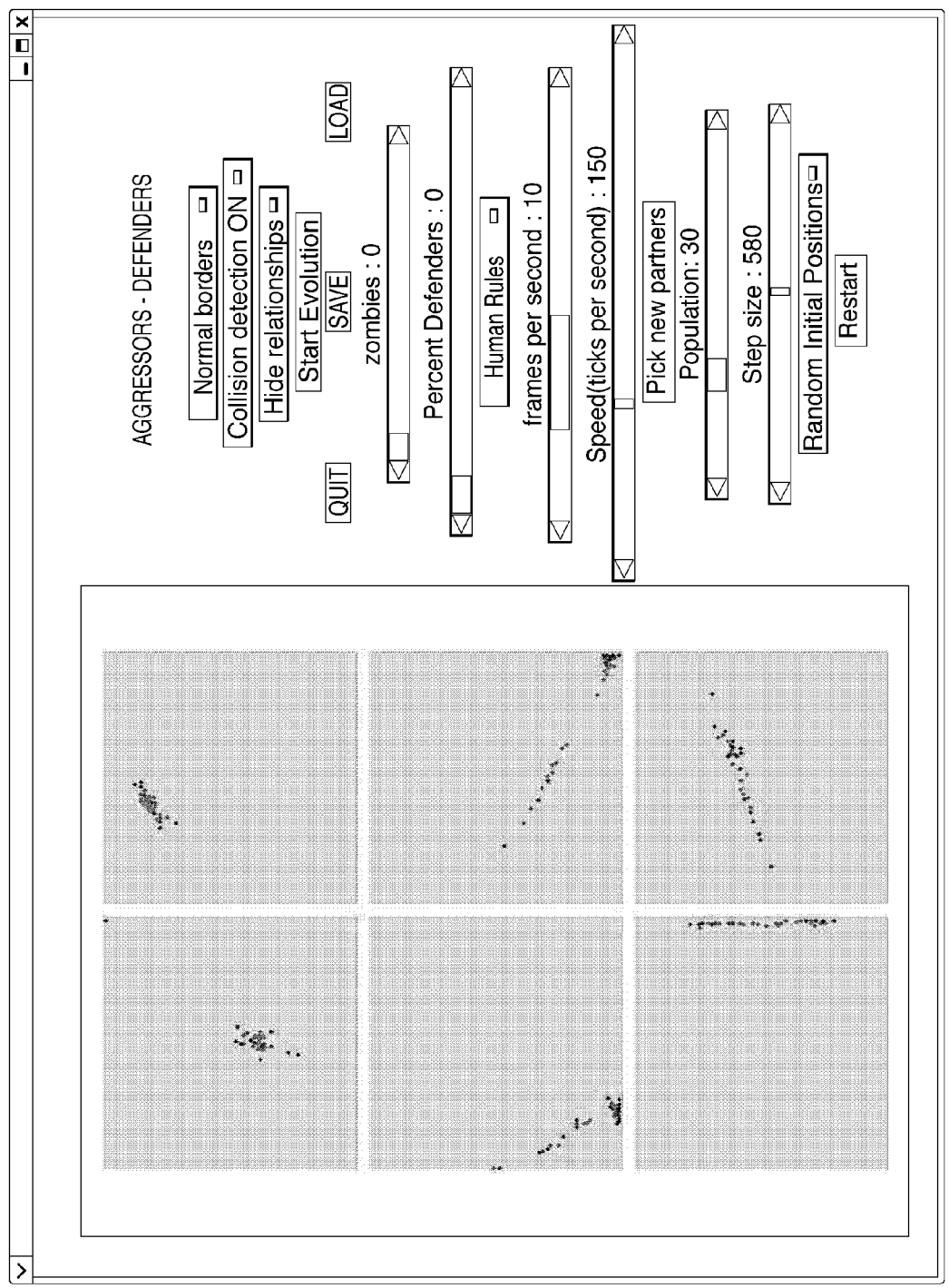
FIG. 5 is a third example of one user interface for one illustrative embodiment of the disclosed methods and systems.

In a parallel embodiment configuration, for example, a user(s) can collectively evaluate the parallel populations and select one of the given parallel embodiments, while modifying objectives. FIG. 5 provides an example graphical user interface for a user based on the described embodiment. For example, the selected parallel configuration/embodiment may represent the embodiment that the user subjectively believes to be approximating a desired collective behavior. In a next generation of the parallel configurations, the selected configuration can remain unchanged, while the rules by which agents in other parallel embodiments act may mutate based on the rule(s) of the selected embodiment, and/or recombinations with a random member of the current generation of embodiments. Accordingly, the determination of a "next" generation is not based on an objective function, but rather, a collective behavior of a selected agent population, as such collective behavior is assessed and selected by a user. The rules to achieve the collective behavior can thus mutate based on such selection. Further, the number of rule iterations/generations can be determined by the user(s) when the collective behavior of the agents satisfies a desired collective behavior as determined by the user(s).

The disclosed methods and systems can also be understood to reflect and/or otherwise be applied to dynamic behavior of the agents. The dynamic behavior can be considered as the changing states or properties of the agents as time passes (e.g., relative to time) where these changing states can be due to other agent and/or environmental characteristics and/or properties (e.g., agent movement).

Another embodiment where ABM modeling is applied concerns financial markets, and accordingly, the disclosed methods and systems are also applicable to such application. In one such embodiment, Interactive Evolutionary Computation (IEC) can be used to discover parameters of an agent-based model of a financial market from aggregate observations of the "true" model. As provided herein, the user(s) can operate a visualization tool to navigate a parameter space using genetic operators. Locations in the parameter space can resolve to a set of parameter values that define traders and their trading strategies, which can generate a synthetic price history. A user(s) can employ the disclosed methods and systems to find a combination of values that can reproduce the target price history. In one embodiment, a java-based model of a financial market can be used, where each model includes order management and clearing mechanisms (e.g., an order book), traders operating trading strategies, a market maker posting orders on the book which are matched with traders' orders, and a price history.

In such an embodiment, a small initial population of ABMs can be generated with random parameter values, with resulting price histories generated by running the models and providing the price histories to the user(s) (e.g., via display). A user(s) can select patterns according to objective and subjective criteria the user(s) may employ in visually comparing the price histories with a target. The user(s) can thus affect the search by configuring genetic operators (e.g., elitism (copied to a new generation), mutation, crossover, percent mutated, proportion/percent crossover versus percent mutation, etc.) to produce a new generation of models based on the user-selected "fittest" solutions in the previous generation. The new generation is simulated, and price histories presented to the user, etc., until the user determines that a price history reflects the target.

In one embodiment, the disclosed methods and systems can be applied to search/analysis/visualization (hereinafter "SAV") models, some of which may combine search with analysis and/or visualization (e.g., clustering techniques), as the space of SAV models can be high-dimensional, and navigating such space manually may not be efficient and may not ensure a satisfactory coverage of models. Nonetheless, it may take several human beings to evaluate each model because of the amount of implicit knowledge, subjective experience, and intuition that may be required for the evaluation. Furthermore, one may not always know ahead of time, for what to look. In a simple example, a first search model might fetch a set of items that are not "interesting" (e.g., "Middle East males younger than 65" returns too many items) while a second search model may return more interesting results (e.g., "Middle East males taking flight lessons" is a smaller and potentially more "interesting" subset); however, determining which search model yields more interesting results is often not obvious beforehand because of the complexity of the data (e.g., that the second search model is more interesting might only appear when the search has been performed, that is, when the model has been applied to the data). Further, different experts might bring a diversity of perspectives to the search model and it may be difficult to leverage such diversity. The disclosed methods and systems can thus reconcile SAV through a large space of models (e.g., potentially thousands or millions of SAV models) with human evaluation of each model, and/or enable users to explore SAV models without full a priori, explicit knowledge of what they are looking for in the data, while allowing participation by more than one expert and/or user.

Accordingly, the disclosed methods and systems can employ IE to guide the exploratory design and testing of SAV models for discovering patterns in data and understanding data. In such embodiments, IE can leverage the knowledge and expertise that is in the form of un-verbalized and/or un-formulated and/or implicit and/or subjective search criteria, where in some situations, experts may not be able to formulate ahead of time (e.g., a priori) for what they are looking, but know that they will recognize it when they see it. Exemplary applications include, but are not restricted to, data mining and data understanding for security, bio-informatics, marketing, consumer understanding, operational analysis or strategic purposes.

Accordingly, and with reference to FIG. 1, the disclosed systems and methods can assist in discovering patterns in data by generating a population of search and/or analysis and/or visualization models 112, applying the models to the data 114, displaying the results for evaluation by one user/expert or a group of users/experts 116, using input(s) from the expert(s) or user(s) 118 to generate a new population of search and/or analysis and/or visualization models 120, and, iterating until an "interesting" pattern is discovered 122 (e.g., as determined by the experts). The generation of the search models may consider a formal objective function and formulated constraints and criteria as well as the multiplicity of subjective criteria. Some embodiments may allow for further interaction of the user, such as provided in the FIG. 2 embodiments.

The exploratory design of SAV models for data mining and data understanding can thus be facilitated by the disclosed methods and systems when the search criteria are not fully known and/or formalized a priori. The evolved solution can incorporate the implicit knowledge, subjective preferences, and satisfy the implicit constraints of the expert(s) or user(s) while alleviating the human energy required to validate the solution before evaluation. The data can be numerical, non-numerical, quantitative, qualitative, deterministic, uncertain, and/or noisy, etc. The nature of the data does not affect the disclosed methods and systems, however, the nature of the data does influence the choice of specific SAV models that can be used.

Accordingly, several solutions can be initially generated either randomly or through some relevant heuristic within a predefined space of solutions, where a solution can be an SAV model. The dimensions of the pre-defined space of solutions can define primitives that can be used to construct SAV models. For example, the space of solutions can be a sub-space of the space of queries that can be formulated using a query language such as SQL, and/or it can be the space of possible same-time correlation functions of the field variables that characterize the data, and/or it can be a space of parameterized visualization algorithms, etc. Constraints can be added by the expert(s)/user(s) so that certain solutions are not presented. For example, a user might want to explore SAV that do not look at temporal correlations beyond one month: models presented to the user will then satisfy that constraint, enabling the user to explore a specific subset of model space without concern for the validity of the generated solutions.

Each of the generated solutions can be applied to the data (FIG. 1, 114) in a variety of ways. For example the SAV models can be applied to a subset of the attributes and/or to a data sample.

As provided herein, several parallel or sequential representations of the outcomes of applying each SAV model to the data can be visually presented to an expert(s) and/or user(s). The expert and/or user can evaluate the displayed results. The evaluation can be performed through direct visual inspection and/or may involve a more complex interaction between each expert or user, and the results obtained with the various SAV models of the current generation. For example, each expert or user may want to manipulate the results, alter the visualization, view the results from different visual angles, etc. Interactive Evolutionary Computation (IEC) allows a broadening of the search space of possible solutions by direct application of each of the expert(s)'s or user(s)'s subjective criteria, implicit knowledge, and preferences to evaluate the results they are presented. Each expert or user assigns fitness values to the various SAV models according to the perceived value or interestingness of the results presented to them.

As provided previously herein, the highest fitness SAV models can be selected to make a new generation of offspring SAV models borrowing from the multiplicity of high fitness SAV models from all the expert(s)/user(s) who opted to assign fitness values in their allotted time frame. In a multi-expert or multi-user context, aggregate of fitness values can be employed. Each expert/user may further modify the existing SAV models "manually" in that the expert/user can alter the SAV models by introducing changes to the models' parameters. Results obtained from user-modified SAV models can then be displayed for evaluation and may either be added to the current generation or discarded by the user.

One or more of the experts/users may also guide the search, by constraining it to certain SAV models that satisfy certain properties, and/or by preventing certain SAV models from being produced, and/or by suggesting modifications to the current generation of SAV models that the user(s) finds more likely to produce higher fitness SAV models, and/or by altering the mutation and/or crossover operators to apply differentially to different parts of the SAV models. A new generation of solutions can be created following an evolutionary algorithm. Genetic operators based on a selected configuration or other criteria (e.g., random recombination) can allow parallel solutions to be generated based on the expert(s)'s or user(s)'s input from the interactive process. As provided with respect to FIGS. 1 and 2, the new generation of solutions can then be presented to the expert(s) or user(s) in an iterative process. The number of generations can be expert/user-determined dependent on the objective and/or fitness function(s), and/or the iterative process may end when a stopping criterion is satisfied.

In another illustrative embodiment, the disclosed methods and systems can be applied to exploratory data analysis (EDA). In a first of such example applications, the methods and systems can be employed to determine and/or evolve two-dimensional linear projections of a dataset to reveal features of high-dimensional data, with evolutions stopping based on the insight a given projection provides into the dataset. In a second example, the disclosed methods and systems can be used to evolve a "true" metric of attribute space by evolving the attribute space distance function until subjectively desired features of the data are revealed when a clustering scheme is applied. In the second of such embodiments, a distance function can be evolved until it produces a compelling cluster using a given clustering scheme.

In the aforementioned embodiments, a small initial population of solutions (e.g., linear projections, or distance functions) can be generated 110-112 and applied to the data 114 (e.g., apply projection to dataset, or apply distance function to dataset and clustering scheme). The results can be provided to the user 116 who can select 118 the subjectively most fit solution(s), and/or assign a fitness value to one or more of the displays. A new population of solutions can be generated using genetic operations 120, and in some embodiments, randomly generated solutions can be injected into the population to provide diversity. The new population's two-dimensional representations can then be computed, etc., with the process iterating until a user specifies a stop condition and/or another condition is satisfied.

Similarly, the disclosed methods and systems can allow one or more individuals to interactively search for an entry in a database when the entry is not known to the individual(s), the search criteria by which the final entry is selected are not known (or expressed), the search criteria rating for the data entry is too subjective to compare multiple entries objectively, and/or relative preferences for the different search criteria are not known, expressed, or changes over time, e.g., during the search. With continued reference to FIG. 1 (and FIG. 2), the disclosed methods and systems can aid the search by generating a population of possible solutions to the search, displaying the possible solutions for evaluation by the individual(s), using input(s) from the individuals(s) to generate a new population of solutions, and employing an iterative process until the individual(s) decides on the final solution. The generation of solutions may consider a formal objective function, formulated constraints and criteria, and the multiplicity of subjective criteria.

The evolutionary schemes can thus facilitate the search of large but finite databases when the search criteria are not fully known and/or formalized ahead of time by incorporating implicit knowledge, subjective preferences, and satisfying implicit constraints of the user(s) while reducing the effort users would have to put into a search with traditional techniques.

In such an embodiment, several possible solutions can be initially identified either randomly or through some relevant heuristic within the predefined space of possible solutions, where a possible solution is an entry in the database. Since the size of the database is finite, the space of solutions is the database. The dimensions of the solution space are the primitives that can be used to identify database entries. For example, the space of possible solutions can be a database of vacation packages, in which the individual solutions are identified by destination, trip duration, price, etc. Furthermore, constraints can be added by the user(s) so that certain solutions are not presented. For example, a user might want to limit the price to a certain maximum value, e.g., vacation packages presented to the user then will satisfy that constraint, enabling the user to explore a specific subset of vacation package space without being distracted by solutions that are, for example, too expensive. Such an embodiment can allow for the aforementioned parallel and/or sequential representations of the possible solutions identified in each iteration (e.g., user is presented with vacation package attributes (destination, price, type of entertainment, educational qualities, opportunities to relax, etc.)) for evaluation through direct visual inspection and/or a more complex interaction between each user and the representations of the possible solutions in the current generation (e.g., result manipulation by altering the valuation for the different criteria, comparing the different solutions from different angles, etc.). As in the other embodiments described herein, each user assigns fitness values to the various solutions according to the perceived value and/or interestingness of the results presented to them.

In one example of an online shopping website for gifts, a user might be looking for a gift, without a specific idea for the gift. In this embodiment, the disclosed methods and systems can assist the user in finding an item by iteratively presenting new possibilities, with the user indicating (e.g., input, ranking) which of those choices are appealing. For example, the website could present the user in the first iteration with a jet ski, a watch, a statue, and a scarf. After indicating which of these items the user prefers, through ranking or some other method, the proposed approach would present in the next iteration, for example, the watch and the statue with a table clock and a credit card holder. By iteratively rating and generating new solutions, the user can search a large database of gift ideas in a directed manner without having to look at/evaluate gift ideas of no interest. Once the user is presented with a gift choice desired by the user for purchase, a selection could place the gift choice into an online shopping basket for later check-out. Once the user is satisfied with the user's choices, the iterative process can terminate and the user might proceed to check-out or simply exit.

In another embodiment, the disclosed methods and systems can be applied to drug discovery, where drug discovery can be understood to be a process of identifying chemical compounds for clinical trials when starting from a broad set of molecules obtained from high-throughput screening (HTS) and/or other technologies delivering entry points for drug discovery programs. In the lead generation phase, the initial set of active molecules obtained from HTS, also called hits, are progressed into lead series by a comprehensive assessment of chemical integrity, synthetic accessibility, functional behavior, structure-activity relationships (SAR), bio-physiochemical and adsorption, distribution, metabolism and excretion properties (ADME). Starting with lead series, lead optimization is aimed at producing compounds that have the desired activity and drugability properties. The sequence from hit to lead series to optimized lead can be important in reducing attrition in the costly clinical phases by intercepting many crucial issues (often ADME- and toxicity-related) before it is too late to resolve them. Despite the availability of numerous computational models that often reliably predict a wide range of molecular properties, chemists are not using such computational tools and there is also a tendency to resort to synthesis more than might be necessary. The disclosed methods and systems can thus enable a multi-disciplinary search for compounds that exhibit a range of desirable characteristics when in practice, the multi-criterion objective function and the constraints may not be known a priori. Accordingly, the disclosed methods and systems can employ the aforementioned interactive evolution principles to guide the exploratory design and testing of compounds to discover compounds with "desired" properties.

Hit to lead optimization (HILO) is commonly understood as an iterative process of selecting molecules from an initial set (hit or lead series), testing their properties either after synthesis or using in silico models, and selecting new, better molecules in several rounds of feedback cycles. Accordingly, with reference to FIG. 2, the disclosed methods and systems can assist chemists and drug discovery experts discover such compounds by generating populations of molecules from an initial set of molecules using automated or user-defined search criteria 210-212, displaying the molecules and some of their calculated or actual properties for evaluation by one user/expert or a group of users/experts 214, using input(s) from the expert(s)/user(s) 216 and/or actual assays after some of the molecules have been synthesized to generate a new population of molecules 218, and continuing as provided in FIG. 2 until compounds with the desired properties (e.g., as determined by the experts/users) are discovered. As in the other embodiments, the user(s) can guide the search for the next generation of molecules by subjectively evaluating the desirability of the displayed molecules and/or by providing manual additions or deletions to existing molecules, such as additions or removals of groups of atoms, by defining search operators based, for example, on the addition or deletions of groups of atoms or based on special-purpose crossover/recombination operators, by forbidding certain molecular types from being generated, by altering or fine tuning the multi-criterion, multi-constraint objective function, and/or by requesting the synthesis of one or more of the displayed molecules or variations thereof for wet testing. In a multi-user/multi-expert context, the collective expertise of the group is aggregated into a coherent discovery and decision-making process.

The systems and methods thus enable HILO experts to interact with the search in various ways, either by evaluating compounds or by defining search operators, by defining the objective function and/or the search constraints, and/or by deciding to synthesize certain compounds whose properties do not appear to be correctly predicted by computational models. In this manner, the multiple, explicit or implicit, search criteria and constraints are considered, thereby restoring the multi-disciplinary nature of HILO, while allowing the integration of the use of computational models (e.g., computational chemistry tools to predict various properties (e.g., activity, selectivity, stability, ADME properties, mutagenecity, etc) of the molecules. Such models can also assess the reliability of their predictions. The user(s) can select which models are executed at each generation. Accordingly, with reference to FIG. 2, user input 216 can include selections of models, parameters for the models, etc.

With continued reference to FIG. 2, in one embodiment, several solutions can be initially generated through some relevant heuristic within a predefined space of solutions, where a solution is a molecule. The first generation of molecules may, for example, result from adding or removing particular atoms or groups of atoms to the starting set of molecules (hit or lead series) at random locations, and/or by applying particular recombination operators to the initial set of molecules. The generated molecules satisfy basic chemical constraints. In addition, constraints can also be added by the expert(s)/user(s) so that certain molecules are not presented. For example, a user not might want to explore molecules that have a particular sub-structure: molecules presented to the user(s) will then satisfy that constraint, enabling the user(s) to explore a specific subset of molecular space without concern for the validity of the generated molecules.

In an embodiment, some molecules can be selected by the user for synthesis and testing. In particular, if the computational models do not appear to produce reliable predictions for certain key attributes, the user may resort to synthesis and run assays to measure the properties associated to the key attributes. The results of the actual assays can be provided to the system as user input 216.

As in other embodiments, several parallel or sequential representations of the molecules (e.g., a 2D and/or 3D display of the molecular structure, results of their evaluations by a range of computational models or actual assays, etc.) and other information/data (e.g., estimated reliabilities of the models' predictions) can be visually presented to each expert(s)/user(s). Accordingly, each expert or user can be presented with several parallel or sequential representations of the molecules and some of their computed or assayed properties. The estimated reliabilities of the models' predictions can also be displayed so the user can decide whether it may be necessary to resort to synthesis.

In one embodiment, the highest fitness molecules can be selected 216 to make a new generation of offspring molecules borrowing from the multiplicity of high fitness molecules from the expert(s)/user(s) who opted to assign fitness values in their allotted time frame. The new generation of molecules can be calculated 218 using genetic operators such as mutation and crossover applied to the selected molecules following a standard scheme such as roulette wheel sampling or other schemes known in the art. Mutation operators can be defined for example as additions, deletions, or substitutions of atoms or groups of atoms. Crossover operators take two molecules and recombine them. Genetic operators allow parallel solutions to be generated based on the expert(s)'s or user(s)'s input from the interactive process.

The particular mutation and crossover operators used to calculate the new generation of molecules can be based on the specific molecular space explored. In an embodiment, the mutation and crossover operators can be defined interactively by the user 216, for example, to explore particular variations of a particular molecular structure. A user may also guide the search 216 by constraining the search to certain molecules that satisfy certain properties, and/or by preventing certain molecules from being produced, and/or by suggesting modifications to the current generation of molecules that the user(s) finds more likely to produce higher fitness molecules, and/or by altering the mutation and/or crossover operators to apply differentially to different parts of the molecules.

It can be understood that a user may alter and/or redefine all or part of the objective function. Because HILO is a multi-criterion process, the user can, for example, modify how different criteria are weighted in the objective function, and/or the softness/hardness of certain constraints 216. For example, at a certain stage in the process, the user may increase emphasis on certain ADME properties and less on activity and selectivity properties. In this configuration of the system, an evolutionary algorithm using user-specified mutation and crossover operators will use the user-defined objective function as the fitness function and will execute automatically, without human intervention for a user-specified number of generations or until a stopping criterion is met (e.g. see FIG. 2). At the end of such an execution, the user can evaluate the molecules generated and may decide to continue with the same objective function and genetic operators for a user-defined number of generations of automated evolution, modify the objective function and/or constraints and/or genetic operators and execute a user-specified number of generations of automated evolution, and/or switch to a more interactive mode where evolution takes place one generation at a time with user intervention between generations; thus, the fitness function can be defined by the priorities given to the objectives, where the appropriate prioritization of objectives may be the unknown. Further, as provided herein, selection of a solution is not based solely on comparison with a fixed objective function, but rather a solution can be based on subjective expert/user-evaluation of the solution (e.g., in this embodiment, a molecule).

In a further embodiment, the disclosed methods and systems can be employed to explore high dimensional data space using sound. Sonification can be understood to be the transformation of data relations into perceived relations in an acoustic signal for the purposes of facilitating communication or interpretation. As in other embodiments, the objective and/or fitness function is a priori mathematically unexpressed, and although a design of a sound may be contemplated, such sound may not be known until it is heard. Such embodiments can be applicable in situations in which visual representations for orienting through data may be limited, and audio cues can be employed to alert a user(s) to details, such as specific patterns or errors that should not be ignored. As the dimension of the data increases, the scalability of sonifying data, rather than visualizing it, can provide benefits.

Sonification can take advantage of a human ear's ability to detect time-sequenced input at a high resolution. The auditory channel can detect specific sequences and trends, and also, an overall display of input versus its individual components (e.g., a listener can often hear an orchestral arrangement as a whole, and/or detect a particular instrument). Sound also creates an effective response which allows people to associate emotions and states to certain types of sounds. Using these responses can make intuitive interpretations of the sound easier.

Additionally, the application of evolving maps whose fitness is determined by their ability to detect patterns in data is amenable to sonification. A map with a specific set of parameters can be translated into a sound(s) which can audibly signify certain features of the data. Time series include one example, such as listening to the stock market by mapping the price to frequency. In data sets of many dimensions, there is no obvious mapping to a visual or an audible display, and model-based sonification can be used to translate from data to sound. The parameter specification and choice of method to navigate through the data aspects of sonfication provide example instances where the disclosed evolutionary algorithms can be employed.

The application of the disclosed methods and systems to sonification includes a process of converting raw data (e.g., time series, clusters, customer satisfaction data, etc.), into sounds. Such a process includes representing a sound mathematically, and it can be understood that a sound may be based on Equation (1):

$$\text{tone} = \alpha \sin(ft) \quad (1)$$

where $\alpha$ is the amplitude of the sound, f is the frequency, and t is the time dependence for creating the sound (e.g., a pure tone is generated by fixing frequency and amplitude). Such tone can be sampled at a sampling rate (e.g., Nyquist rate) to provide for a digital sound that can be used by a processor-controlled system such as a computer.

FIG. 6A shows a tone displayed as a spectrogram, with the horizontal axis representing time, and the vertical axis representing frequency. Adding multiple sine waves, or tones, creates more complex sounds. FIG. 6B shows a spectrogram using multiple tones. This particular method of synthesizing sounds can be referred to as "additive synthesis,", and can be represented mathematically by Equation (2):

$$\text{tone}(t) = \alpha_t \sin(f_t t) + \beta_t \sin(\phi_t t) + \delta_t \sin(y_t t) \quad (2)$$

As may be known, genetic programming can be used to represent a parse tree that contains terminals and operators and can be decoded to create a processing scheme. GP is usually implemented so that the processing scheme returns or provides a number. For example, a GP function "add(sin(mul (a,b)), sin(mul(a,c)))" can be decoded to a parse tree shown in FIG. 7A. In this example, time and each data column are mapped directly to GP terminals, and using this mapping, GP can create a range of sounds and non-sounds. A less flexible option is shown in FIG. 7B. Here the data columns are pre-processed with a time multiplier into a sine wave before being passed to GP terminals. Although less flexible, this option provides a narrower search that biases towards listenable outputs.

Further, we can also consider the terminals in GP to be populated with data which can bias the search (e.g., GP) in the direction of creating audible sounds. For example, data could be preprocessed into time varying sine waves before being provided to the GP. A GP processing scheme could then use an addition scheme to replicate additive synthesis.

It can be understood that the disclosed embodiments can be applied to raw, numeric, and/or qualitative data; however, if the data is small in magnitude, a mapping to sound amplitude could provide inaudible results. Further, the data mapping can consider providing data for an audible range. Such considerations can be provided as soft constraints which can be implemented using a preprocessing scheme which maps the mean of the data to a selected frequency, and distributes the other data accordingly. For a time-series, data can be mapped to a frequency after scaling. Other techniques for time-series include mapping of data to a moving average, differencing, and a percentage change, with such examples provided for illustration and not limitation.

When preprocessing clustered data, aspects/characteristics of the cluster may be of interest (e.g., tight/spread cluster, location with respect to other clusters, etc.). Distances between clusters may be determined using, for example, a Euclidean measure and/or absolute distance, across dimensions. FIGS. 8A and 8B provide respective examples. Additive Synthesis can be used once cluster data has been evaluated in GP to allow the listener to analyze the data a cluster at a time.

Embodiments can also include a post-processing (i.e., after the GP scheme evaluates the pre-processed data), in which data is made audible. Such post-processing can include a shifting of data to accommodate the audible range. FIG. 9 shows examples of some possible post processing routines.

As with the other embodiments provided herein, human feedback can be provided, which can include choosing sounds which exhibit interesting qualities for finding patterns in data. Through the aforementioned iterative process (e.g., FIGS. 1 and 2), a map can be built which accentuates the areas of the data in which the user is most interested. Accordingly, in one embodiment, a user(s) input(s) can indicate to the GP which function(s) to keep in the next generation. The GP can create new versions of the map using mutation and crossover, which accept the pre-processed data as input. Mutation in GP can include modifying a branch of the parse tree, or replacing a current sub tree with a newly created one. Crossover can include creating a new 'child' tree by combining sub trees from two parent GP functions. In some embodiments, pre-processing schemes can also be evolved to provide a broader search.

Figure 10:
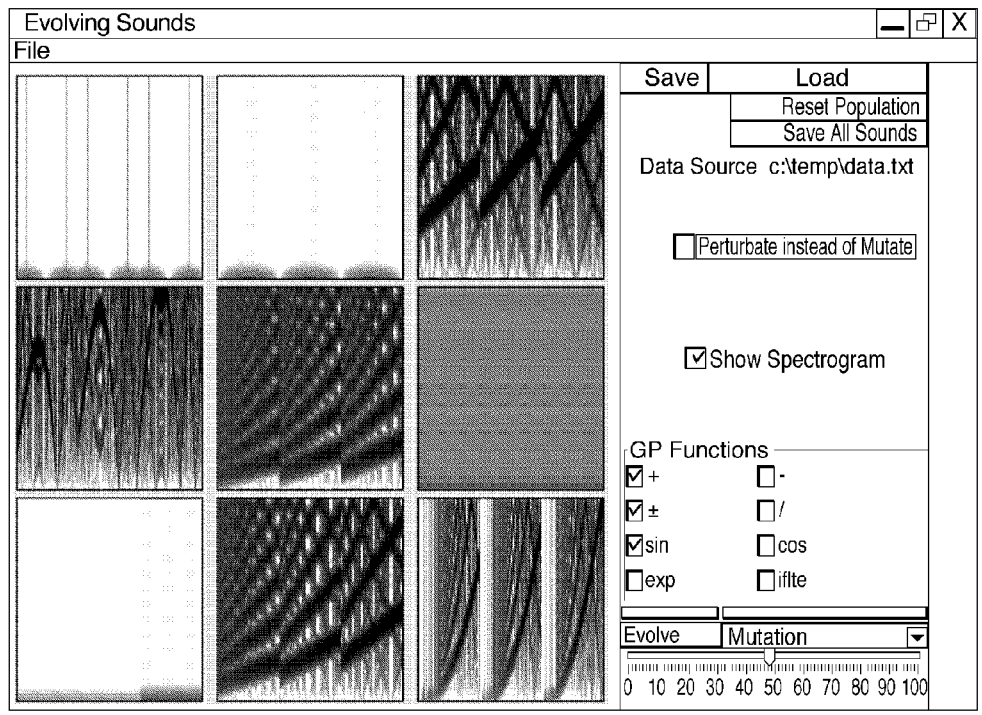
FIG. 10 illustrates a sample GUI for a sonification embodiment.

In an example embodiment of the sonification embodiment, a user(s) can select a data file as input and/or elect for a number of clusters to be generated with specified standard deviations and centroids. The user can also see a visualization of the results of the sound function as a spectrogram of the output sound file. The operators available to the example GP (+, −, *, sin, etc) are selectable from a GUI (e.g., see FIG. 10).

The combination of operators selected by the user(s) can be used in future mutations and/or newly created functions. In the illustrated embodiment, the user can specify whether full mutations are performed or perturbations of existing trees (e.g., make small changes to existing functions, rather than create and/or delete sub trees).

Figure 11:
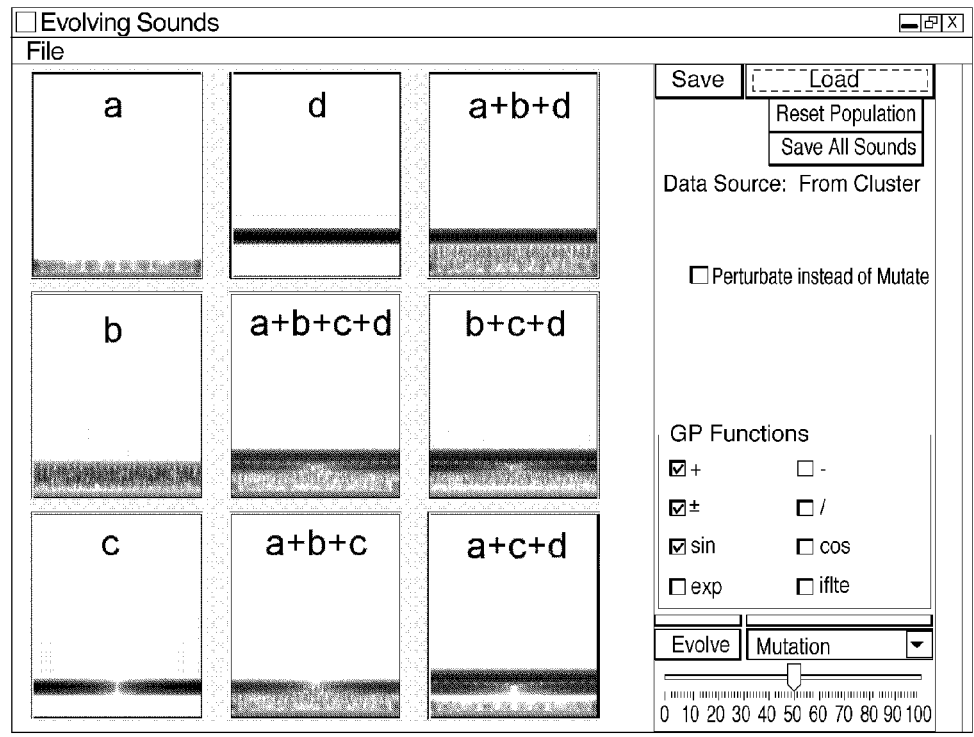
FIG. 11 is an example GUI providing sonified multi-dimensional cluster data.

An interactive GUI can be demonstrated by creating data with one cluster having a Gaussian distribution in multiple dimensions. Results are shown for two and four dimensions of data. With reference to FIG. 11, the spectrograms of several different functions are shown, with four dimensions in the cluster, labeled a, b, c, and d, with these spectrograms showing each dimension sonified by itself as a pure time varying sine function. Since the dimensions in this example are created using different distributions, the sound of each dimension will differ. The other spectrograms show combinations of dimensions using Additive Synthesis. The dimensions selected in each function are shown by the equation indicated on the spectrogram. Accordingly, because each dimension has a different sound and can be heard when combined with other dimensions, four or more dimensions can be analyzed through sonification. By interactively evolving functions that allow for the addition, subtraction, etc., of dimensions, the user can learn about the qualities of the cluster and can focus on combinations of dimensions. Sound filters can be used and evolved to eliminate noise and other aspects of the data that is not useful for analysis.

In a further embodiment, the disclosed methods and systems can be used to provide an Interactive Evolutionary (IE) tool for Portfolio Management. An assessment of a portfolio can be difficult, and hence, can be described as having an objective function that may be understood to be a priori mathematically unexpressed. Portfolio management can be understood to include efficient distribution of resources required by the entities in the portfolio. Such entities can entail projects (e.g., industrial, developmental, etc.) and/or investments (e.g., paper, real estate, etc.), which are assumed to have uncertain outcome/pay-off (e.g., positive, negative, degree thereof), although the methods and systems are not limited to such definition of portfolio management, or such entities.

With reference to FIG. 2, as with other embodiments, independent parameters can be defined 210, which can be understood herein to include, but not be limited to, genotype representation, objectives, and constraints. Although the management of a portfolio of projects is provided here as an example, the proposed approach is not limited to this example and can be applied to other portfolios of entities requiring some form of resources. The presumed problem then may include of a set of projects having a certain number of sequential and parallel tasks associated with them that require a specified number of different resources. Upon completion of tasks associated with one project, that project is said to have a certain payoff that may vary, depending on the timely completion of a project and other uncontrollable factors. Since projects generally require some of the different resources, at any given time there are not enough resources available to service the projects at the same time. The problem in managing this portfolio of projects thus includes assigning the available resources to achieve the highest amount of payoff based on the entire portfolio. In the illustrated embodiment, payoff is not limited to a monetary value, but includes objectives such as maximum market penetration, highest quality reputation, and minimal time to market.

Using the aforesaid terminology, in this example, the independent parameters are the start times of the projects' tasks, the objective functions are the monetary payout after project completion, time to market, quality reputation, and market share, and the constraint functions/schemes are the levels of availability for the different resources. The choice of a genotype representation can vary with the specifics of the portfolio and its entities, but in the present example, the genotype can include a variable length chromosome of real values depicting the start times for the tasks, i.e., a collection of the independent variables. As with the other embodiments of the disclosed methods and systems, genotype representation can be based on the embodiment, and can include fixed length, variable length, binary string, matrix, problem specific (e.g. some specific structure of values and logical statements), floating-point vector, permutations, symbolic expression/tree structure (GP), and others, with such examples provided for illustration and not limitation.

Continuing with the basic framework of FIG. 2, a user(s) can next present input(s) 216 by processing displayed information, and communicating preferences for objectives, features of interest in particular portfolios or entities, whether specific variable values should be held constant in future iterations, parameter settings the EA should run with in the next iteration (e.g. a condition that identifies the end of the EA iteration), and/or whether specific portfolios should serve as parents for the next generation. Specifically the latter types of feedback could also be construed as "fitness" information about the portfolios that can otherwise not be calculated. Accordingly, information displayed to the designer(s)/user(s) can include data for the objective functions and design variables, and because such data is likely multidimensional, some display options can include cluster analysis and display, slide bars for design variables for components of a design alternative, objectives information in form of Pareto frontiers, spider charts, joint and univariate probability plots, prediction profiles, and/or constraint analysis. The display for the illustrated example could include graphs that inform the portfolio managers of resource utilization, total yearly payout, and average project time to market, with such graphs allowing for comparison of the different portfolios presented to the managers. Another display could include a drill down capability of looking at portfolio specifics to understand resource allocation and advancement of projects. An example display could include task start times and project work distribution over time, so that the portfolio manager(s) can express opinions about observed portfolio features. Such input, as provided previously herein, can include parent selection for the EA, objective preferences for the automated alternative evaluation procedure, and/or a guided search for a portfolio with specific features, and/or objective preferences, features of interest, specific independent variable values, evolutionary algorithm parameters, parent solutions, and/or end of iteration condition (e.g., number of generations).

As also provided herein, input consolidation techniques and/or schemes can be used, and can be understood in one embodiment to include voting and/or scoring schemes. For example, group individuals can independently decide on their preference for alternatives, which can include voting without preference structure (e.g., spot vote), single vote, limited vote, and/or cumulative vote. In one embodiment, voting with preference structure (e.g., preferential vote) can be employed, including simple majority and pair wise comparison (e.g., condorcet principle). In some embodiments, all individual alternative objectives can be used to form one group decision, and where an ordinal approach is employed, such methods can use an agreed criteria/borda score approach. Similarly, a cardinal approach, such as a utility/weighted sum approach, TOPSIS, and/or JPDM can be used.

Utilizing the information provided by the portfolio managers 216, a new population of potential portfolios can be generated 218. The variation operators used to comprise the new population can impact the efficiency of the EA's search. For example, if the operator is chosen in poor correspondence to the representation and fitness function, it may be awkward to relate the variation operator to the distance metric of the fitness landscape. General variation operators can include:

Mutation (Normal, Cauchy, Uniform)
    For example: 15% probability to mutate given chromosome at ten genes, new gene value chosen from uniform distribution over entire variable range
Crossover
    For example: 100% probability to do simple crossover with one random splice point
Replace parent solutions
    For example: parents are discarded after crossover or mutation
Keep parent solutions
Weighted average
Permutation
Specific to representation (matrix manipulation)

With continued reference to FIG. 2, population members can be evaluated 220, and for the EA to distinguish between the different population members, the alternatives can be evaluated in terms of the objectives and constraints using numerical analysis. In one embodiment, the EA can utilize an integrated analysis tool that allows for timely evaluation of portfolio alternatives, although other tools can be employed. Such analysis tool can calculate problem-specific objective and constraint function values based on the independent variable setting(s). For example, the tool can calculate objective values for monetary payout after project completion, time to market, quality reputation and market share, and resource requirements for the constraints based on the start times of the project tasks in each portfolio evaluated. As in this example, whether a particular portfolio can be deemed "good" or "bad" can be judged many times only through a multitude of characteristics, i.e. objectives. Depending on the portfolio of entities to manage, such objectives can vary from utilization of available resources, to maximum return on investment, to other non-monetary qualities the portfolio entities might have.

Once each population member's constraint and objective values are determined 220, a subset of alternatives, as defined by the portfolio managers' preferences, can be identified 222. With such large population sizes, it can be impractical and unnecessary to subject the portfolio managers to the entire (large) population. It is therefore proposed to down-select the population prior to presentation. This down-selection can be based on the fitness values assigned to the portfolios under evaluation, e.g., picking from a list of ranked alternatives, or be fitness calculation free, such that an interesting set of solutions could be the Pareto frontier itself, or alternatives dominated by at most one other population member.

Since for most portfolio management problems, the fitness of a portfolio is based on the satisfaction of multiple objectives, a variety of approaches to fitness assignment or fitness-free selection can be employed for the disclosed interactive evolutionary process. Established MOGA methods as Goldberg's Pareto ranking, a utility function method with weights representing the relative preferences for the objectives, Branke's Focused Pareto Frontiers, Deb's Goal Programming adaptation, Parmee's Fuzzy Preferences, and/or uses of TOPSIS, LINMAP, and MinMax/MaxMin, could present a useful solution.

In some embodiments, when using the utility function approach for the implementation example, objective function values, monetary payout after project completion, time to market, quality reputation, and market share, can be normalized, multiplied with their respective preference weight, and summed to one fitness value for each portfolio. In the case of Goldberg's Pareto ranking, non-dominated portfolios in the population can be assigned a Rank Number 0. Non-dominated refers to a condition of a portfolio in which no other portfolio can be found that has better values for monetary payout, time to market, quality reputation, and market share. When assigning Rank Number one, Rank Number zero portfolios can be disregarded when identifying the remaining non-dominated portfolios. This process continues with progressively higher Rank Numbers until the entire population has been assigned a rank.

While solutions with good fitness values are desired, such solutions cannot be considered a final solution, as long as they violate the identified constraints. For the implementation example, a penalty approach can be used that diminishes the constraint-violating portfolio's utility function fitness by a certain percentage, e.g., twenty percent, or increases its Rank Number by one or two for the Pareto Ranking approach. As a consequence, those portfolios that violate constraints would appear to be less desirable as feasible others with similar fitness; however, they could still be more desirable than some feasible portfolios with very poor fitness. In this manner, some of the "good" genetic material for the "good" constraint-violating portfolios can be preserved for the next generation, hopefully identifying solutions that have a high fitness and satisfy the constraints.

A condition for determining whether the ending of an iteration can be evaluated 224. This condition, specified by the portfolio managers, can vary from reaching/satisfying a number of generations this iteration was supposed to entail, to reaching/satisfying a specified fitness or objective function level, to reaching/satisfying a specified minimum "distance" between portfolio alternatives, guaranteeing a diverse population. Once the condition is satisfied, the set of interesting solutions is (possibly) further reduced to a display set 214. Otherwise, new parents can be selected for the EA's next generation 226.

Determining new parents 226 can include determining, based on the fitness of each population member and/or the designers' feedback, which solution participates in the creation of the next generation, and which solution has to leave the pool of useful solutions. The following includes a list of popular selection mechanism choices:

($\mu+\lambda$)
($\mu, \lambda$)
Elitism
    For example: elite size: two, best fitness
Proportional probabilistic
    For example: the better the fitness the higher the probability of selection for crossover
Tournament method For design problems with a large number of objectives, it is possible that the set of interesting solutions, e.g., a set of Pareto optimal solutions, is large. In such cases, a further down-selecting of the alternatives to be displayed can be performed 214. Some example down-selecting options may use cluster analysis, displaying a representative alternative that is central with respect to objectives or design variables, and/or selecting a fixed number of alternatives with highest fitness to be presented to the portfolio managers.

As provided with respect to FIG. 2, the process ends 228 with the portfolio manager(s) selects a solution that subjectively satisfies the manager(s)'s requirements best.

The disclosed methods and systems can further be employed in the area of image processing. As an audio signal data exists in the time domain, 2D images exist in a two-dimensional spatial domain. In one embodiment, a continuous function for an image can be described as a(x,y), where a is the intensity of the image at location x,y. Digitally sampling the image results in a matrix [m,n] of intensity information where m and n are the image height and length in pixels. The size of the matrix is equivalent to the resolution of the image. A higher resolution sampling results in a more precise image representation but also a larger store of information. Image intensity, or amplitude, is a number, often from 0 to 255. This can be a single number for grayscale images or multiple numbers. For example, an RGB coded image has three values to represent red, green, and blue. A image containing 23 bits of information, or 256×256×256, can contain 16 million colors.

Image filters are used for aesthetics, analysis, restoration, archival, and other reasons. Processing is needed on images to reduce artifacts, repair color and/or illumination after down-sampling, resolution enhancement, feature enhancement, and for other creative reasons. Filters are also useful in encryption, compression, and communication of digitized signals.

There are generally three types of filters: point, local, global. A point filter changes a pixel based on the value of the pixel, a local filter modifies a pixel based on its neighborhood, and a global filter modifies a pixel based on statistics from an entire image. Arithmetic filters can be applied to single or multiple images as input. Sample arithmetic filters are AND, OR, XOR, add, subtract, and multiply. For example a scaling can be performed on an image where each pixel's value is multiplied by 0.9, to decrease the intensity of the image. A scalar of 1.2 can provide a brighter image. Scaling an image by a number can be applied to a pixel overall, or applied individually to the color components of a pixel.

Convolution is a local filter that changes the intensity of a pixel based on its neighbor pixels. Convolution can be used for blurring, sharpening, edge detection, embossing and other effects. A convolution filter uses a kernel matrix to act as a window on the pixels around a location. The kernel is an (m×n) matrix of numbers used to create weighted average of the pixels around the location. Typical 3×3 convolution kernels are shown in FIG. 12, and a sample output image processed by such kernels is shown in FIG. 13. Although the illustrative convolution kernels are (3×3) matrices, the disclosed methods and systems are not limited to such size. Convolution can also be used as a local filter by multiplying the identity matrix by a value.

A lookup filter is another image operation that involves creating a lookup table for each byte (0 to 255), and substituting values from the image using the table. This can be used for low pass filters, color reduction and compression, and various artistic effects, amongst other uses.

The disclosed methods and systems can be used for filter creation, as many users of such filters (e.g., digital image enhancement software users, etc.) may not understand the complexities generated by applying a single, and/or multiple sequential filters, to an image.

Figure 14:
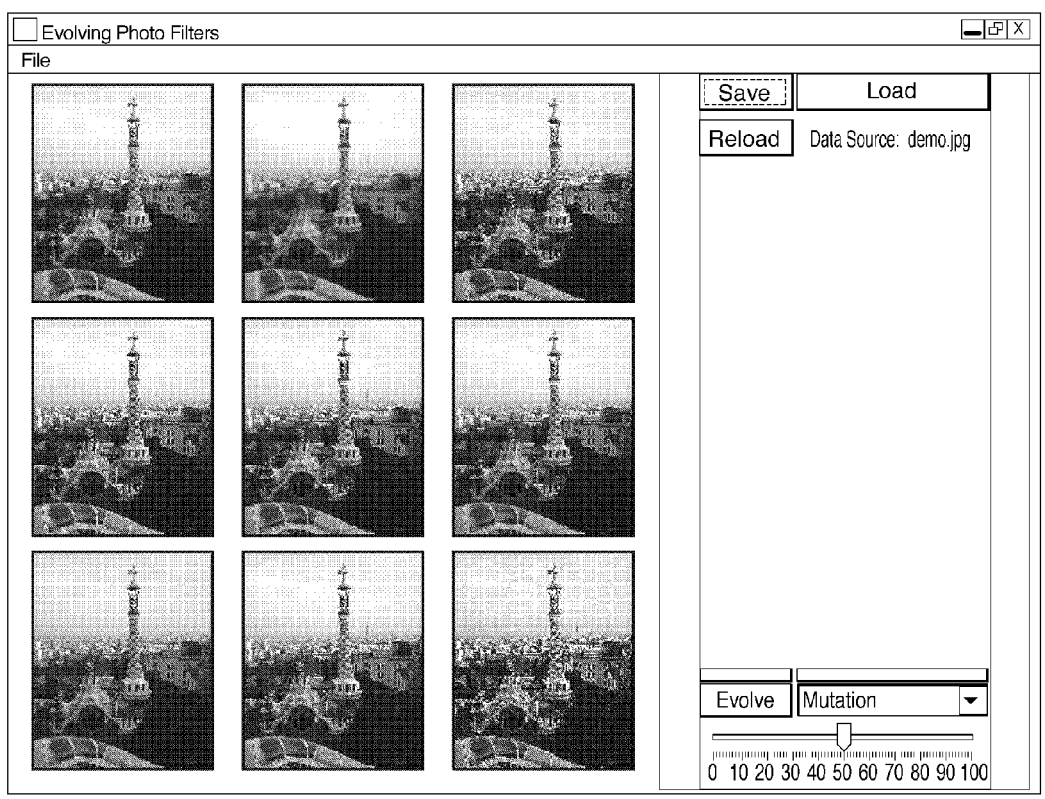
FIG. 14 provides an example GUI for an image processing embodiment.

An interactive algorithm, here implemented as an application (e.g., set of processor instructions), can be created to allow a user to interactively select filtering operations to perform on an image, and the sequence and parameters for those filters. This application does not require user knowledge about image processing or filters. Instead of specifying a specific set of filters to be used, the user can be presented with a set of images created from computer generated filters, and the user can be prompted to select an image that most matches a desired output. The application can then create, using a genetic algorithm (GA) as provided herein, a new set of images based on the favored image, and present the new set to the user. As provided throughout this disclosure, this iteration can continue until the user is satisfied with the result, and thereafter, the user can save the filter and/or the resultant image. A screenshot of one GUI for a sample application is shown in FIG. 14.

As provided herein, in a standard GA, a population is evaluated for fitness and evolved. The members of the population are judged based on their phenotype, i.e., their characteristics or behaviors. The phenotype for an individual is encoded via their genotype, which for a genetic algorithm is similar to a "digital DNA" or a set of parameters that describe the traits of the individual. Historically, a genotype was represented as a string of ones and zeros that would be decoded to the final phenotype. Any type of number can be used in a genotype. For this application, a set of floating point numbers and integers can be used. Each number represents a specific parameter for the image filter.

The descriptions of the genes in a sample implementation of this evolutionary algorithm (EA)/GA are shown in Table 1.

TABLE 1

Image Processing Genotype

| Gene Name | Description | Sample Values |
|---|---|---|
| Operation Selections | A sequenced list of operators to perform | {Convolution, Rescaling, Recoloring, Blurring, Sharpening, etc.} |
| Scale | A multiplier for each pixel in the image | 0.5 to 4.0 |
| Offset | An offset amount to add to each pixel in the image | −150.0 to 150.0 |
| Sharpen Amount | A multiple of the identity matrix applied to a standard sharpening convolution kernel | 5 |
| Blur Amount | A multiple of the identity matrix applied to a standard blurring convolution kernel | .1 |
| Individual Scaling Amounts | The same as scale above but for individual color components (e.g., RGB) | 0.5 to 4.0 |
| Convolution Kernel | An M × N matrix (usually 3 × 3) for custom convolution operations | −10 to 10 |

Each individual of the population can be generated (FIG. 2, 218) with random values within certain constraints. When the user selects 216 one image for mutation, the function for that image is used to create M×N−1 offspring 218. Mutation is applied to the function by modifying each gene with a certain probability. Accordingly, a random number is created for each gene and if the number is below a mutation rate probability, then that gene is selected for mutation. Once a gene is to be mutated, it can be multiplied by a Gaussian random number multiplied by a sigma specific for that gene. Each gene can have its own sigma value since some values should change more gradually than others. The sigma values for the genes can be scaled by an overall mutation sigma parameter.

Crossover can be performed when the user selects two parent images. The filter functions for those images can be combined by randomly taking genes from one of the two parents to compose an offspring.

After each generation of mutation or crossover 224, a user is presented 214 with a series of new images based on new filter functions. The user can evaluate the images based on a comparison with a predetermined output (e.g., another image). If the user has no predetermined image quality in mind, the tool can be used to create new ideas and explore the filter search space. In this way, the disclosed methods and systems assist the user in the creative process by interactively presenting new ideas based on suggestions from the user.

A variation on the illustrated GUI can include a slider-type input for the user that increases or decreases the mutation amount. Other variations, as provided throughout the disclosed embodiments, should be evident.

What has thus been described are methods and systems that include generating a solution set based on an evolutionary scheme in which an objective function is a priori mathematically unexpressed, presenting data based on the solution set to one or more users, receiving at least one input from the user(s), the input(s) based on the user(s)'s evaluation of the presented solution set, and, based on the input(s), using at least the evolutionary scheme and the input(s) to generate an updated solution set, and repeating the presenting and receiving. It can be understood, as provided previously herein, that different aspects and features of the various embodiments presented herein, can and may be employed in other of the disclosed and non-disclosed embodiments, and thus, features of the disclosed methods and systems may be represented by one or more of the exemplary embodiments.

The methods and systems described herein are not limited to a particular hardware or software configuration, and may find applicability in many computing or processing environments. The methods and systems can be implemented in hardware or software, or a combination of hardware and software. The methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted.

As provided herein, the processor(s) can thus be embedded in one or more devices that can be operated independently or together in a networked environment, where the network can include, for example, a Local Area Network (LAN), wide area network (WAN), and/or can include an intranet and/or the internet and/or another network. The network(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus can be configured to communicate via wired or wireless communications with other processors, where such one or more processor can be configured to operate on one or more processor-controlled devices that can be similar or different devices. Use of such "microprocessor" or "processor" terminology can thus also be understood to include a central processing unit, an arithmetic logic unit, an application-specific integrated circuit (IC), and/or a task engine, with such examples provided for illustration and not limitation.

Furthermore, references to memory, unless otherwise specified, can include one or more processor-readable and accessible memory elements and/or components that can be internal to the processor-controlled device, external to the processor-controlled device, and/or can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

References to a network, unless provided otherwise, can include one or more intranets and/or the internet. References herein to microprocessor instructions or microprocessor-executable instructions, in accordance with the above, can be understood to include programmable hardware.

Unless otherwise stated, use of the word "substantially" can be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun can be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, can be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. For example, it can be understood that the genetic operations can be multiple and/or varied, and different parameters associated with such genetic operations can be provided as input by a user/expert. Further, although user input was specified in the illustrated embodiments of FIGS. 1 and 2 as occurring at a certain instance, input from the user can be provided at multiple stages (e.g., at initialization, problem definition, etc.). Further, the disclosed embodiments can employ the use of randomly generated solutions in addition to those derived from user selection. In multi-user embodiments, for example, the formulation of the solution can be partitioned amongst several users, with different users influencing the solution in a different manner. For example, an employee(s) may provide subjective input on solutions, however a manager(s) may apply/specify (additional) constraints on such solutions.

Any additional changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. In a computer system having a user interface including a display and an input device, a method, comprising:
   generating a set of candidate molecules based on an evolutionary scheme in which an objective function to determine a fitness of a candidate molecule is a priori mathematically unexpressed,
   presenting on the display data based on the set of candidate molecules to at least one user,
   receiving through the input device at least one input from the at least one user, the at least one input based on the at least one user's evaluation of the presented set of candidate molecules,
   based on the at least one input, using at least the evolutionary scheme and the at least one input to generate an updated set of candidate molecules, and
   repeating the presenting and receiving.

2. A method according to claim 1, where presenting data based on the set of candidate molecules includes selecting at least one candidate molecule from the set of candidate molecules to present.

3. A method according to claim 2, where selecting the at least one candidate molecule includes selecting based on at least one constraint.

4. A method according to claim 2, where selecting the at least one candidate molecule includes selecting based on at least one calculated property of the at least one candidate molecule.

5. A method according to claim 4, where selecting the at least one candidate molecule further includes selecting based on at least one calculated property of the at least one candidate molecule satisfying at least one condition.

6. A method according to claim 1, where presenting data based on the set of candidate molecules includes presenting a molecular structure of at least one candidate molecule of the set of candidate molecules.

7. A method according to claim 1, where presenting data based on the set of candidate molecules includes presenting at least one calculated property of at least one candidate molecule of the set of candidate molecules.

8. A method according to claim 7, where presenting data based on the set of candidate molecules further includes presenting at least one calculated value of at least one of an adsorption property, a distribution property, a metabolism property and an excretion property, of at least one candidate molecule of the set of candidate molecules.

9. A method according to claim 1, where the at least one user input includes at least one of: a rank of a plurality of candidate molecules in the set of candidate molecules presented, a rating of a plurality of candidate molecules in the set of candidate molecules presented, a selection of at least one candidate molecule in the set of candidate molecules presented, a modification of a structure of at least one candidate molecule in the set of candidate molecules presented, a selection of at least one feature of at least one candidate molecule in the set of candidate molecules presented, an identification of at least one parent for a genetic algorithm, at least one constraint, a modification of at least one constraint, at least one condition, a modification of at least one genetic operator, and a specification of at least one genetic operator.

10. A method according to claim 1, further comprising modifying at least one candidate molecule of the set of candidate molecules presented based on at least one input from the at least one user.

11. A method according to claim 1, where using at least the evolutionary scheme and the at least one input to generate the updated set of candidate molecules includes:
   generating a population based on the evolutionary scheme and the at least one user input.

12. A method according to claim 11, where using at least the evolutionary scheme and the at least one input to generate the updated set of candidate molecules further includes:
   applying the population to at least one data set.

13. A method according to claim 11, where using at least the evolutionary scheme and the at least one input to generate the updated set of candidate molecules further includes:
   generating the updated set of candidate molecules based upon at least one calculated property of at least one member of the population.

14. A method according to claim 1, where using at least the evolutionary scheme and the at least one input to generate the updated set of candidate molecules includes:
   based on whether at least one condition is satisfied, iteratively using the evolutionary scheme and the at least one user input to generate the updated set of candidate molecules.

15. A method according to claim 14, where the at least one condition includes a specified number of generations of the evolutionary scheme having elapsed.

16. A method according to claim 1, where using at least the evolutionary scheme and the at least one input to generate the updated set of candidate molecules includes:
   using a genetic operator to generate the updated set of candidate molecules.

17. A method according to claim 16, where the genetic operator includes at least one of: crossover, and mutation.

18. A method according to claim 17, where the genetic operator is applied to modify a structure of at least one candidate molecule in the set of candidate molecules.

19. A method according to claim 1, where the method is terminated based on a user input.

20. A method according to claim 1, where the method is terminated based on at least one property of at least one candidate molecule in the set of candidate molecules satisfying at least one condition.

21. A method according to claim 1, where the instructions to the computer system to perform the method are communicated to a processor over a network.

22. A method according to claim 21, where the network is a local area network.

23. A method according to claim 1, where the at least one input from the at least one user is received over a network.

24. A method according to claim 23, where the network is a local area network.

25. A method according to claim 1, where the data presented on the display is transmitted over a network.

26. A method according to claim 25, where the network is a local area network.

* * * * *